United States Patent [19]

Carroll

[11] Patent Number: 4,515,165
[45] Date of Patent: May 7, 1985

[54] APPARATUS AND METHOD FOR DETECTING TUMORS

[75] Inventor: Robert Carroll, Gainesville, Fla.

[73] Assignee: Energy Conversion Devices, Inc., Troy, Mich.

[21] Appl. No.: 302,443

[22] Filed: Sep. 15, 1981

Related U.S. Application Data

[63] Continuation-in-part of Ser. No. 118,639, Feb. 4, 1980, abandoned.

[51] Int. Cl.³ .............................................. A61B 5/00
[52] U.S. Cl. ................................... 128/664; 128/665
[58] Field of Search .................... 128/633, 664, 665; 364/413, 414, 415

[56] References Cited

U.S. PATENT DOCUMENTS 4,286,602  9/1981  Guy ..................................... 128/665
4,290,433  9/1981  Alfano ................................. 128/665

*Primary Examiner*—Kyle L. Howell
*Assistant Examiner*—Francis Jaworski
*Attorney, Agent, or Firm*—Lawrence G. Norris

[57] ABSTRACT

A device and method for the detection of tumors in human and animal tissue using transmission or reflection of nonionizing radiation, in particular, visible light having a wavelength most advantageously in the range of 400 to about 700 nanometers, and infrared light having a wavelength in the range of 700 nanometers to about 4 microns (4000 nanometers). Measurement of the amount of absorption and scatter in regions of the tissue involved is in a scanning mode to produce a shadowgraph image using either single wavelength grey scale or preferably multispectral multiple wavelength false color imaging techniques. The apparatus and method also advantageously can be used in conjunction with computer image reconstruction similar to that employed in computerized axial tomography of the type used in X-ray diagnostic techniques. In one of its more advantageous aspects, the apparatus and method are used to differentiate between benign and malignant human breast tumors.

51 Claims, 26 Drawing Figures

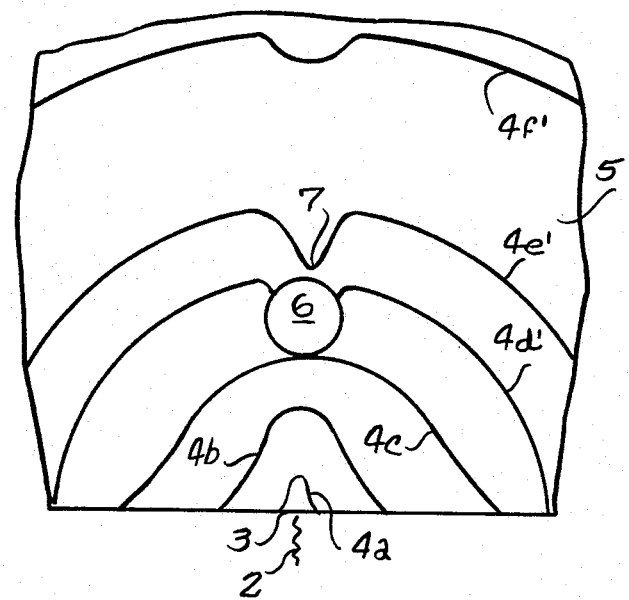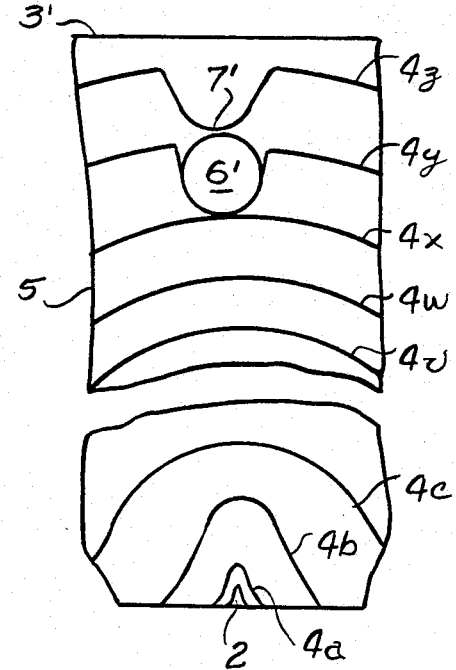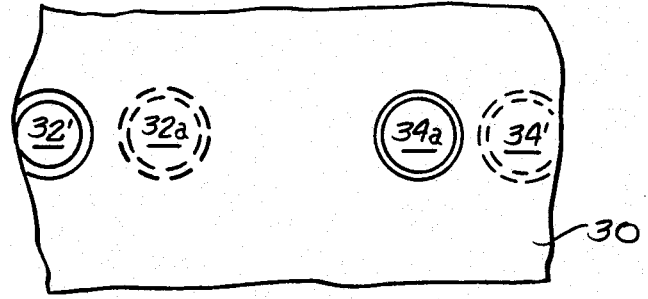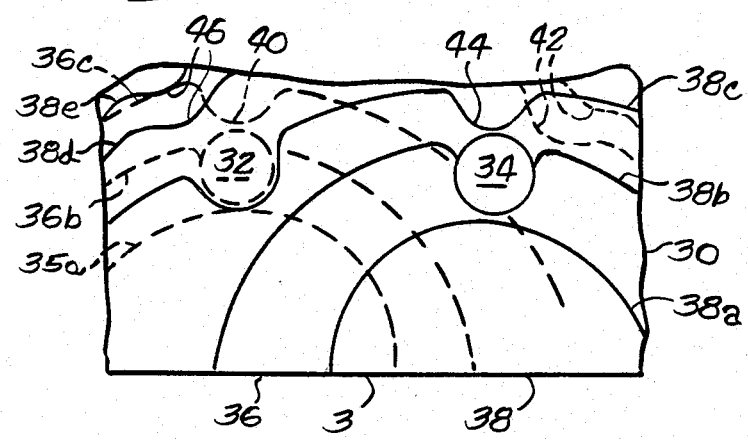

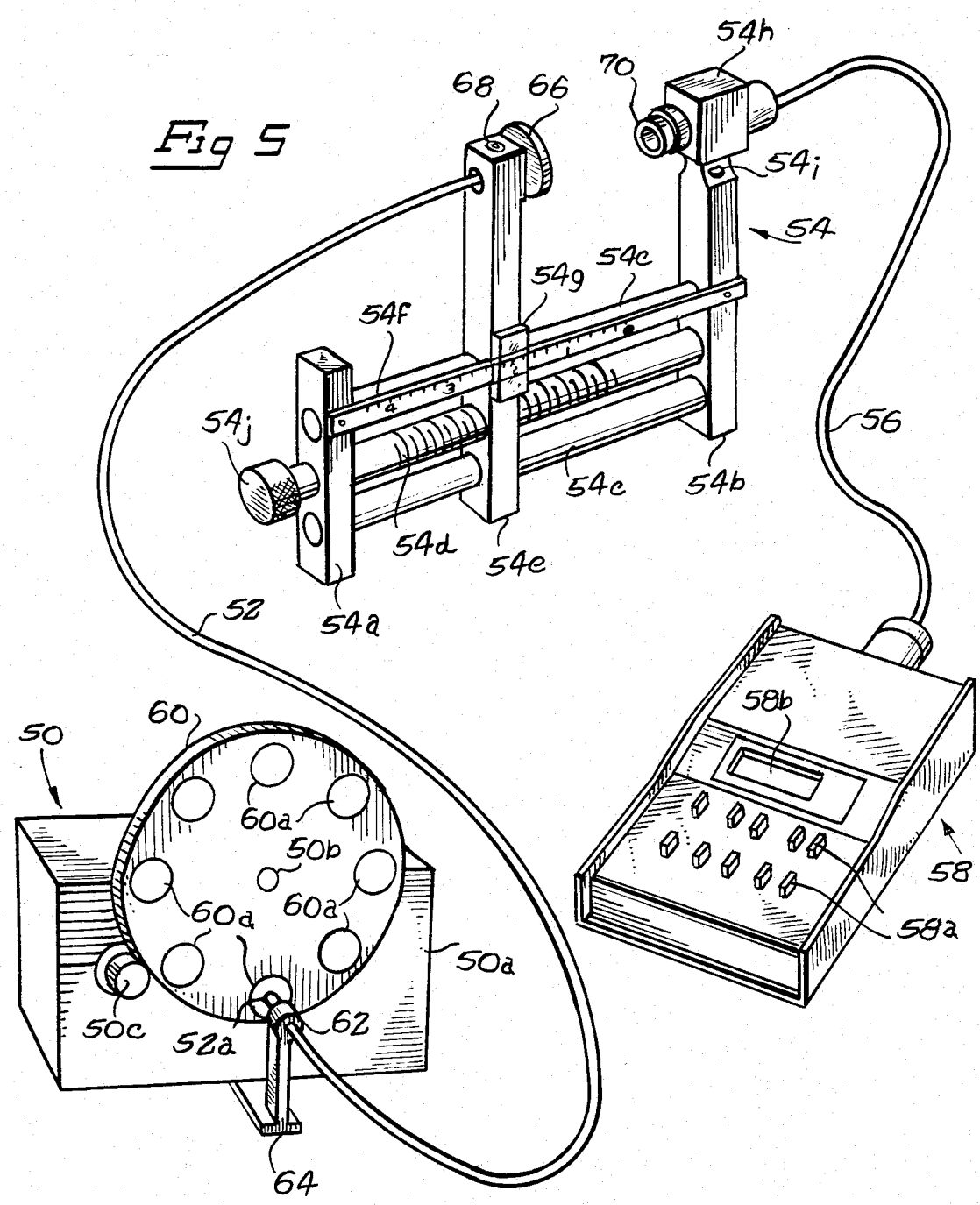

Fig 8B
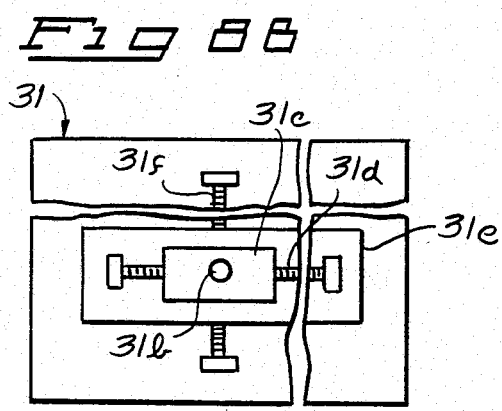
Fig 8A
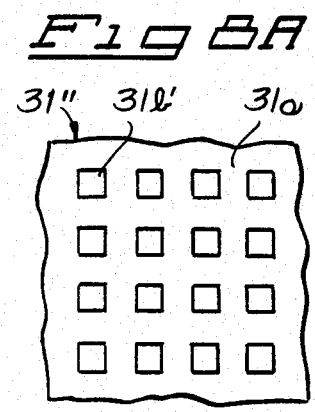
Fig 9B
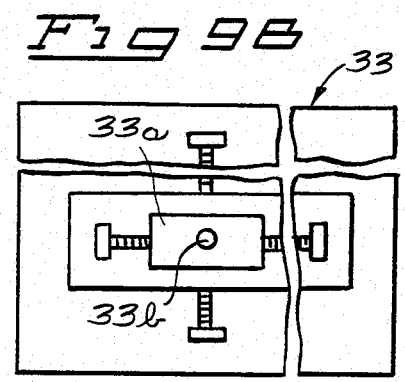
Fig 9A
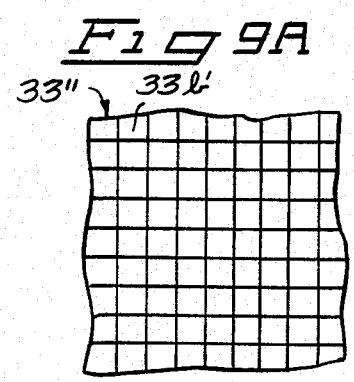
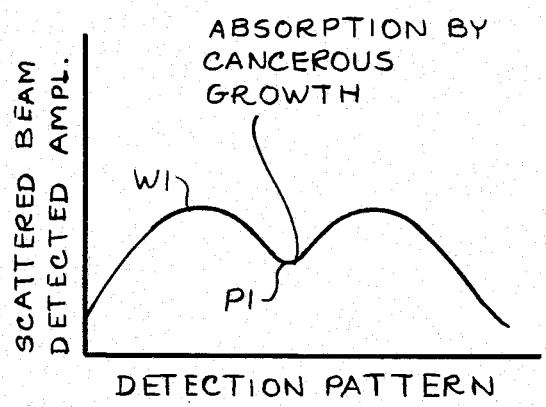
Fig 10A
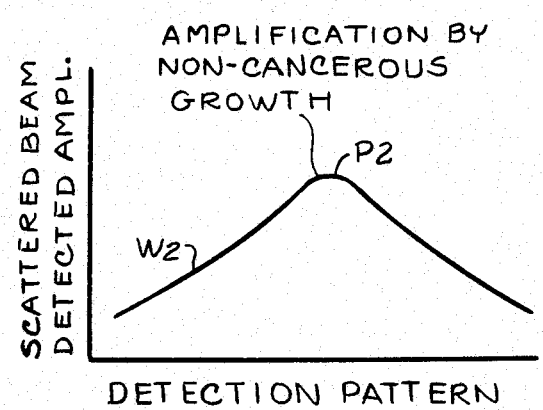
Fig 10B

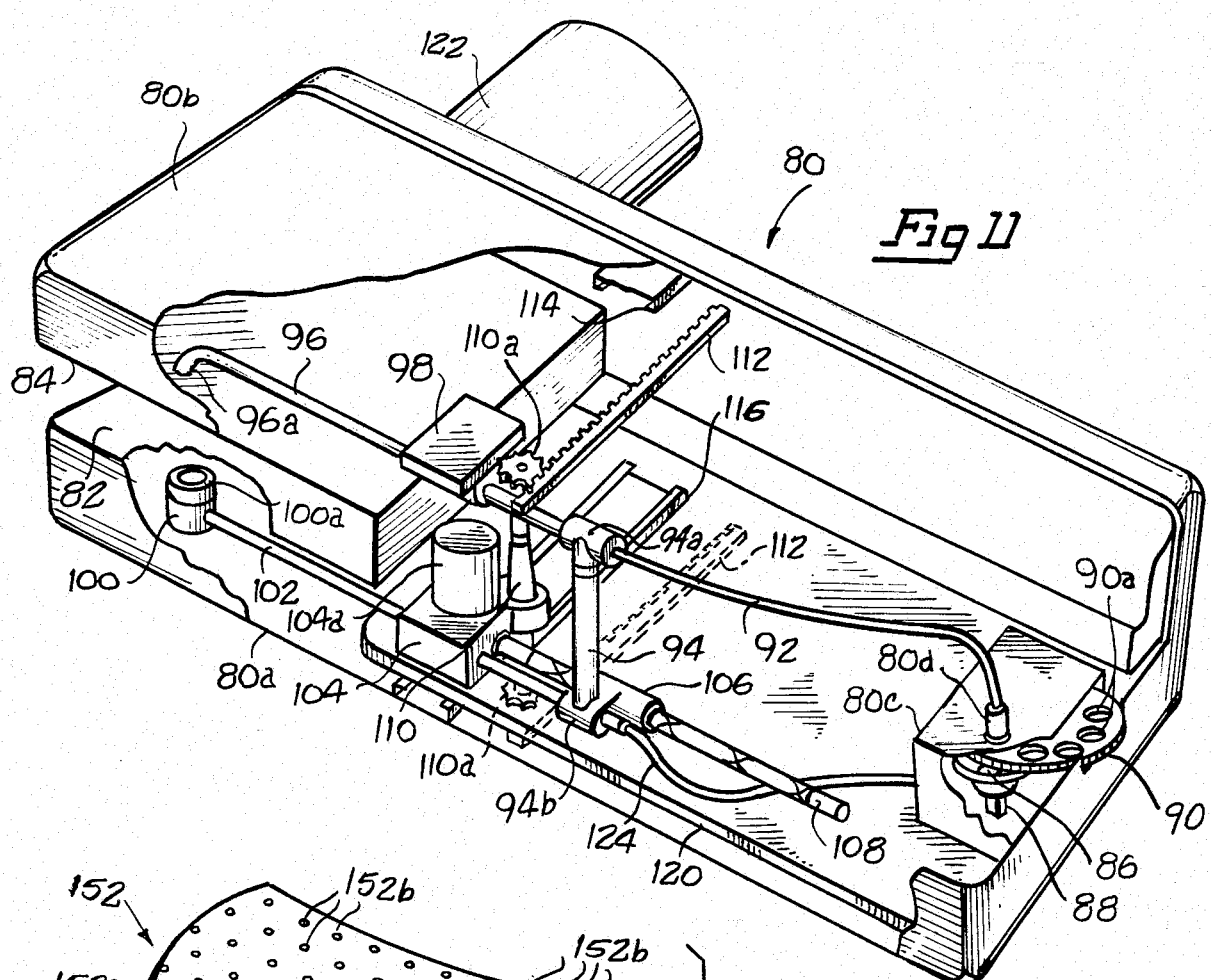
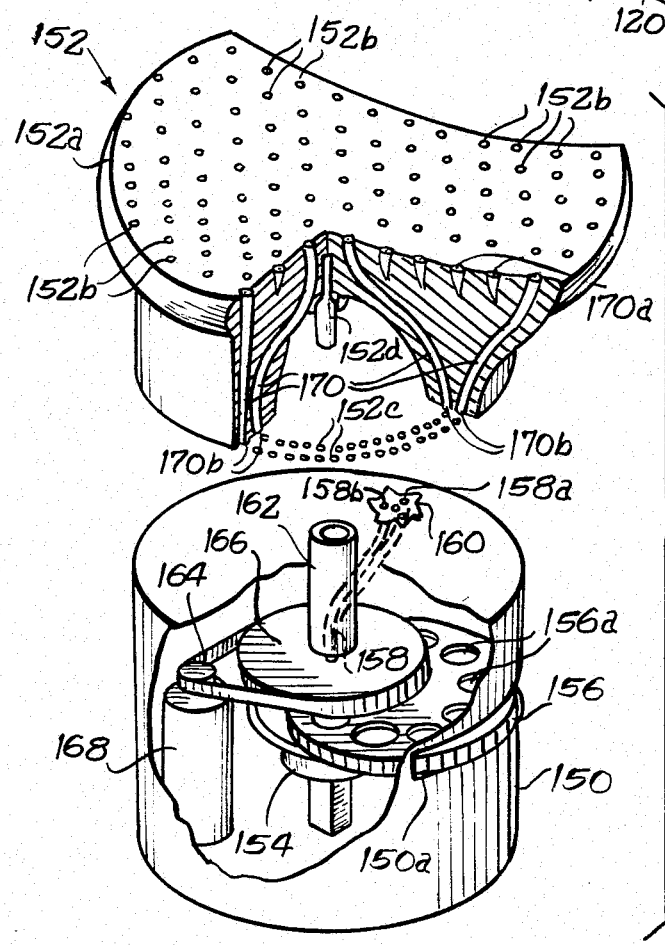

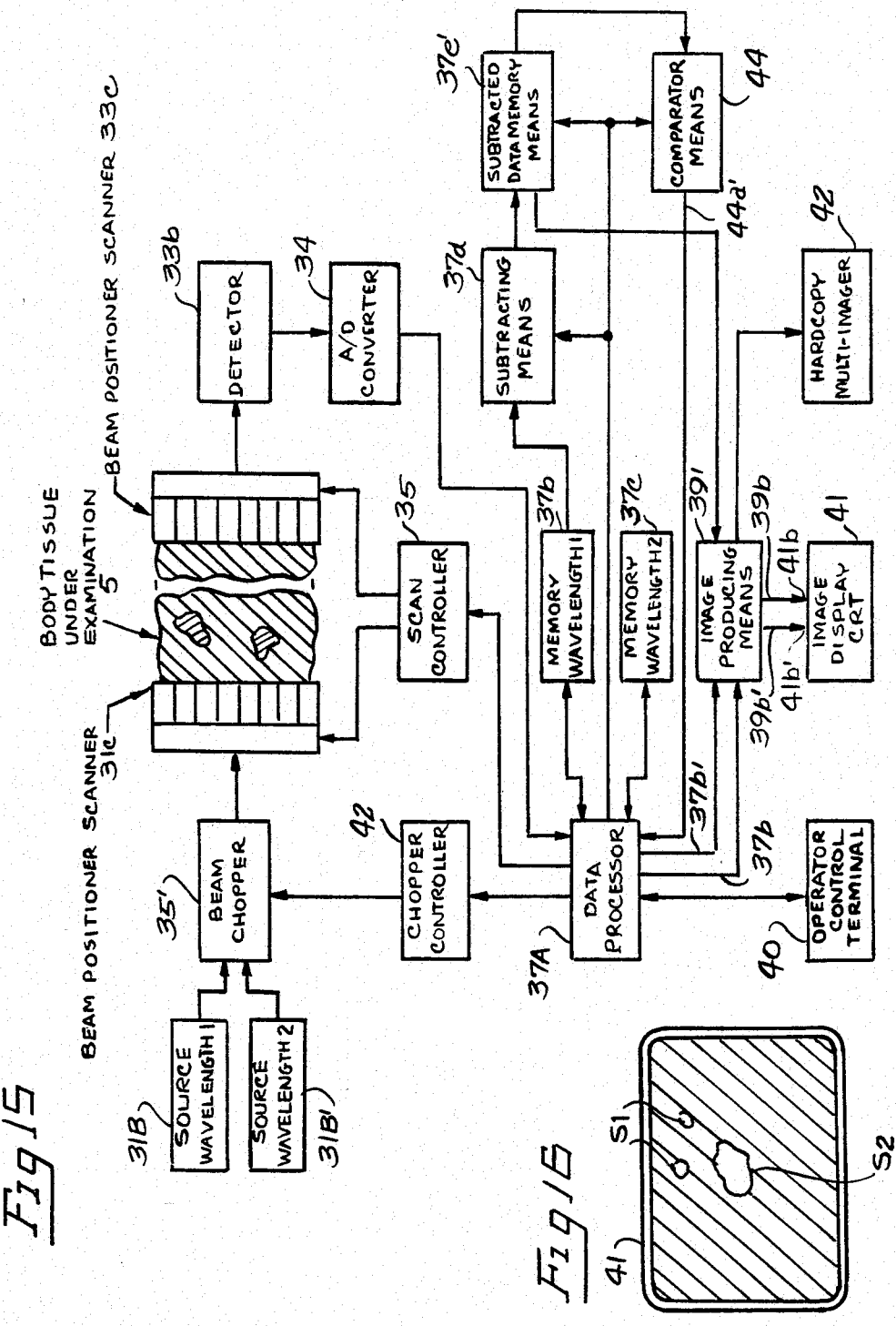

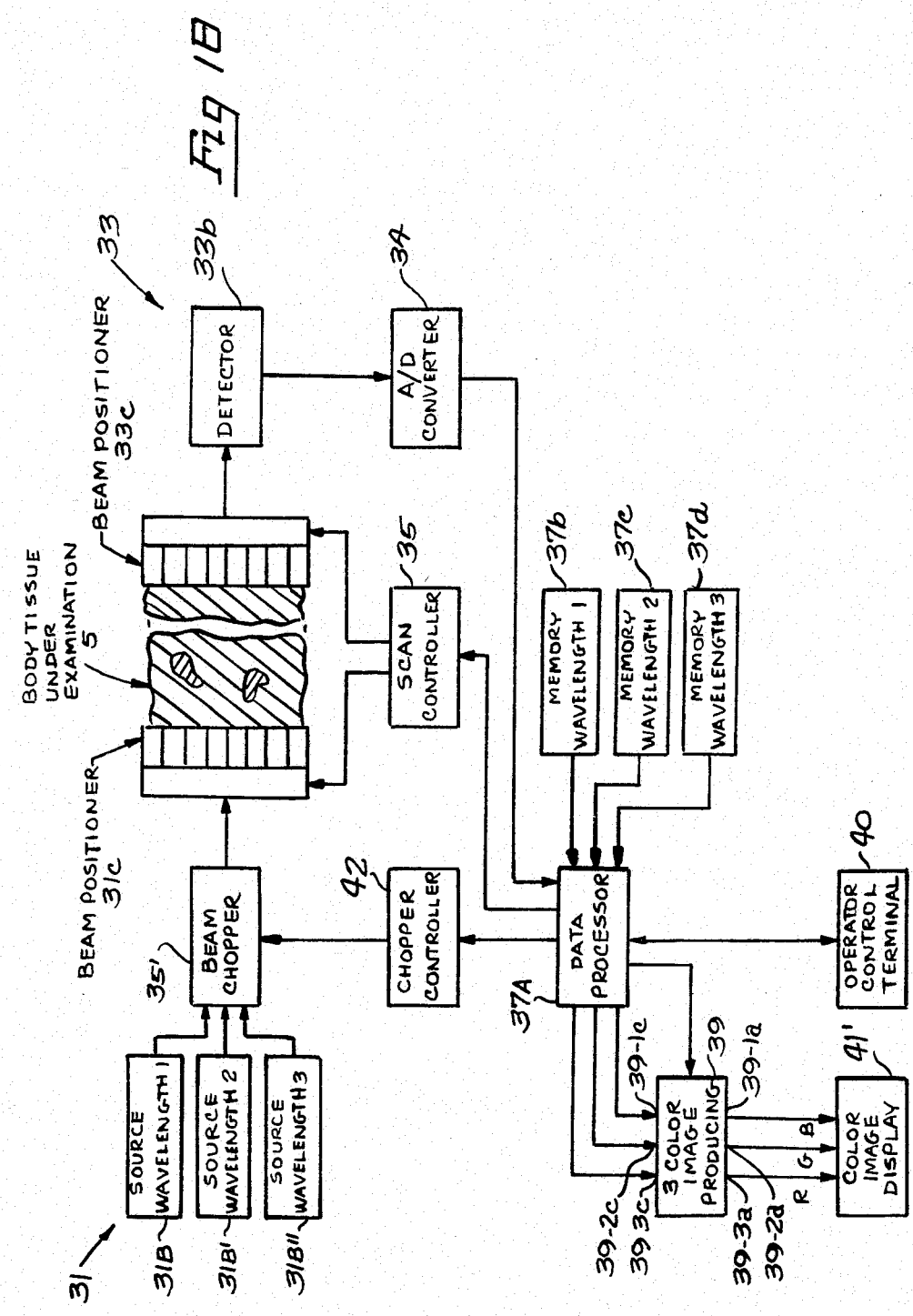

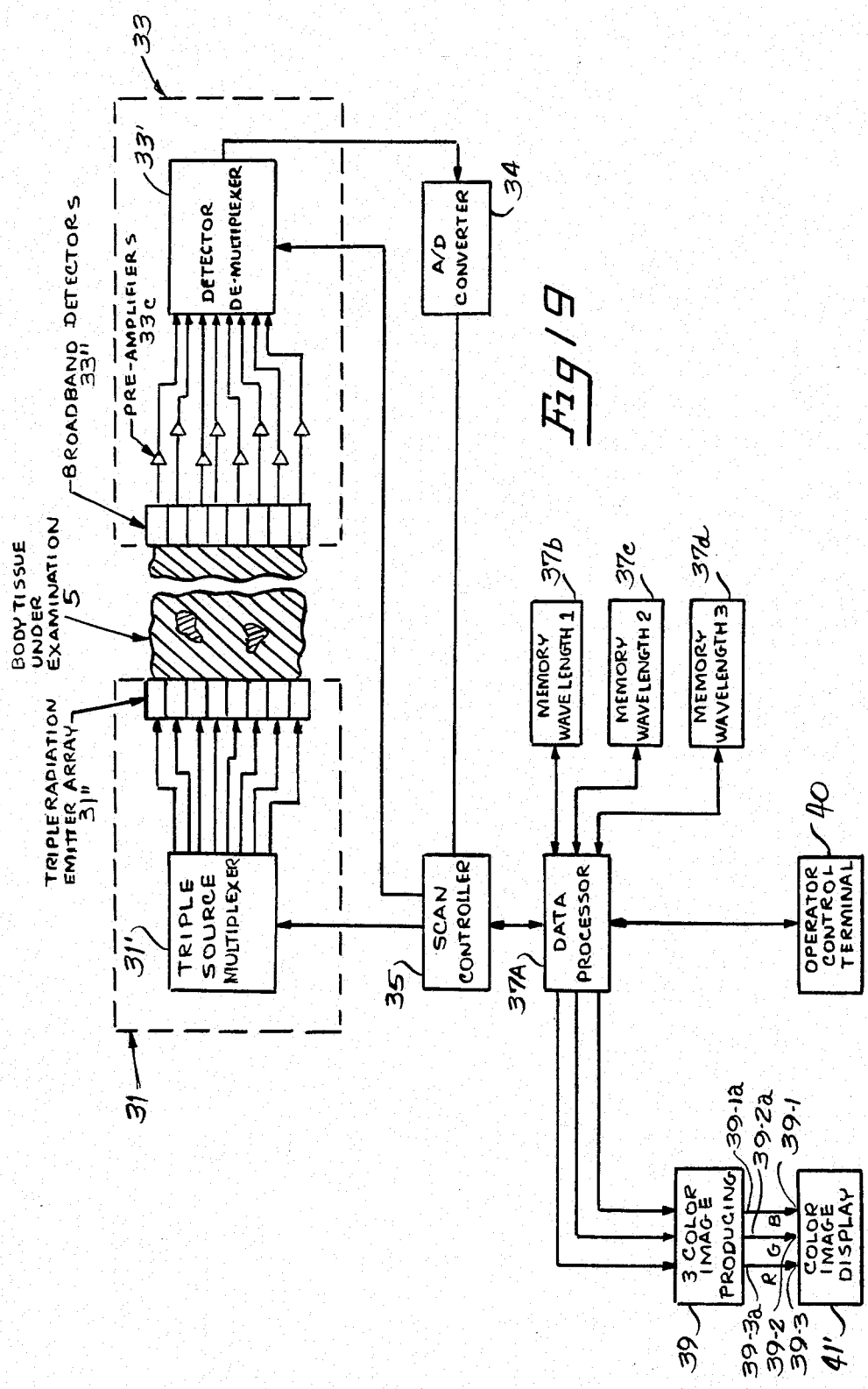

APPARATUS AND METHOD FOR DETECTING TUMORS

RELATED APPLICATION

This application is a continuation-in-part of U.S. application Ser. No. 118,639, filed Feb. 4, 1980, now abandoned.

BACKGROUND OF INVENTION

The present invention relates to a device and method for the detection of and differentiation between cancerous and noncancerous tumors in human and animal tissue, and especially in human breasts where the invention has its most useful and important application.

Present methods of interrogating human tissue to detect the internal structure underlying the skin have employed various x-ray, computerized axial tomographic x-ray, thermographic, and ultrasonic wave techniques. While x-rays yield good images of internal body structure, they rely on ionizing radiation which entails a carcinogenic risk to the patient. This risk is of special importance in the detection of breast lesions. Wholly apart from the radiation dosimetry risks associated with the use of x-rays, the utilization of x-rays is poor in terms of tissue contrast and provides no physiological information.

The use of thermographic techniques in the interrogation of human tissue, which detects the differences in temperature in the different tissue types in the body portions examined, uses infrared radiation detectors to detect the different degrees of infrared radiation emitted by heated bodies. Thermography has a number of shortcomings which make it unsatisfactory as a diagnostic tool, particularly in the case of human breast lesions. Thus, thermography has the disadvantage of being unable to detect and locate small non-palpable lesions in the thick living tissues such as the human breast because insufficient infrared radiation is generally emitted by such small bodies to enable the infrared sensing unit of such equipment to detect any appreciable difference in tissue temperature caused by such small bodies. Temperature fluctuations in overlying skin are large relative to the small temperature difference arising from a tumor. Thus, in the case of breast lesion detection, thermography, alone, generally is not relied upon, and is usually used in conjunction with x-ray mammography. Poor contrast and minimal physiological information are the fundamental shortcomings of thermography. Thus, thermography has been generally discredited as a diagnostic technique because of the very faint signal generated by tumors as compared with the much greater noise signals caused by temperature fluctuations generated by the overlying skin.

Ultrasonic techniques are limited in application by attenuation and interaction of ultrasound waves with the tissue being interrogated. Differentiation of cystic from solid lesions is the primary utility of ultrasound. In addition, ultrasound poses certain biological hazards such as platelet aggregation which is exhibited at power levels less than those causing thermal injury. The primary limitation of ultrasound is poor image quality.

In summary, ionizing X-rays produce good quality images of well developed tumors without adequate substantial contrast differentiation between cancerous and non-cancerous tumors and between such tumors and normal tissue, ultrasound produces fair to poor images and thermography produces only very poor images thereof.

SUMMARY OF THE INVENTION

My invention is based on the production of images using visible and infrared radiation whose degree of absorption and scattering varies both with the functional state of tissue as well as the structure thereof. Thus, because visible and infrared radiation absorption characteristics are quite different in oxidized and reduced blood, one can produce images with such radiation which readily differentiate between oxygenated blood and deoxygenated blood containing tissue. In addition to imaging the oxidation status of the blood, one can also image the oxidation status of the intracellular enzyme cytochrome $a,a_3$. Use of such radiation to produce images differing in intensity with the metabolic state of tissue produces images of much greater contrast between tissue containing blood in its oxidized and reduced states and between such tissue and other tissue such as fat than that obtainable with x-rays. It is characteristic of cancerous tumors that they contain a larger blood supply than that found in fat and it is significant that malignant tumors commonly contain deoxygenated blood while benign vascular tumors commonly contain oxygenated blood. Thus, of great importance is the discovery that common benign breast tumors, such as fibroadenoma tumors, allow much more visible and infrared radiation to pass through them than would pass through an equivalent thickness of normal fatty breast tissue. Thus, common breast cancers with low transmission of such radiation can be readily differentiated from common benign breast tumors with high radiation transmission relative to surrounding normal tissue.

Thus, in accordance with my invention, a method and apparatus for detecting tumors using visible and infrared radiation is provided which can more effectively detect cancerous tumors in the early stages of their formation, particularly in female breasts, than can x-ray and other techniques, and eliminate the hazards involved in the use of x-ray techniques. It should be clearly understood that my method and apparatus invention which externally applies such radiation to the portion of the body involved is fundamentally different from thermography which is passive imaging of infrared rays given off by the body.

While it was discovered many years prior to the present invention that near infrared radiation is absorbed in different degrees by fat and human cheek, to my knowledge no one has heretofore suggested or appreciated that such radiation could be used to detect the differences between cancerous tumors, on the one hand, and non-cancerous tumors and normal healthy tissue, like breast tissue, on the other hand, or that such radiation could be effectively used to produce shadowgraphs or similar images. Thus, it has been well known that the direction of a visible light beam through a human appendage, such as a finger, results in the light beam being absorbed and scattered in such a manner that no useful shadowgraph is obtained of even the finger bone, let alone of blood vessels anc cancerous or non-cancerous tumors therein.

For many years physicians have applied a flashlight bulb directly to the surface of the breast and observed with their eyes on the far side of the breast the pattern of light transmission. Usually, this approach would only detect the presence of large fluid filled cysts if they were present. This practice, called transillumination, is of minimal diagnostic utility. The vast majority of the visible light emitted by the flashlight bulb is absorbed by blood in the capillaries of the breast. The small amount of light which traverses the breast, is in the near infrared wavelengths, where the human eye is very insensitive.

There are two fundamental problems in forming images by visible or infrared radiation transmission through breast tissue. The first problem is that of poor visual detectability by the human eye. This problem is solved by the use of silicon and other photodetectors. The second and more fundamental problems result from the intense light scattering which occurs in tissues. The object blurring effects of scatter can be minimized by scanning the tissues one point at a time and measuring the radiation transmitted at a point directly opposite from the radiation input point. Other features of the invention to be described minimize the object blurring effects of tissue scatter. Moreover, as above indicated, it was not heretofore appreciated that there would be any significant difference in the absorption of visible or infrared radiation by cancerous and non-cancerous tumors, so that the use of such radiation could differentiate between cancerous and non-cancerous tumors, even if images thereof could be obtained. Accordingly, the various applications of visible and infrared radiation applied to various parts of the body heretofore have not been used in a manner to produce images, which generally requires that the radiation source involved scan areas of the body involved. Rather, such sources have been used in various ways by directing a stationary radiation beam against a portion of the body and detecting the magnitude of the radiation received, either on the opposite side of the body portion or on the same side thereof where the radiation source is located, and by measuring the amount of radiation traversing or reflected from the portion of the body involved. Often, such measurement is compared with a measurement obtained by utilizing a reference radiation source having the same or different wavelength directed into the body portion involved. For example, U.S. Pat. No. 4,223,680 discloses a near infrared detection system which utilizes near infrared light sources simultaneously directing stationary near infrared beams into the head of a patient, and a radiation detector detecting the magnitude of the radiation reflected from the brain, which measurement is indicative of the degree of oxygen sufficiency in the grey matter of the brain. Similar techniques have been utilized to determine whether or not blood flowing through a blood vessel has oxidized or reduced hemoglobin, as disclosed in many patents on ear oximeters.

My cancer detection invention is best carried out if the part of the body involved is scanned by either a single physically moving visible or infrared radiation beam, or by the beams produced by a plurality of stationary visible or infrared radiation sources covering the area of the body to be examined. In the latter case, the sources are sequentially activated or otherwise made to direct such a beam against different points on the skin surface involved. The size of the beam or beams used to scan is much smaller than that usually produced by such radiation sources. The scanning beam may have dimensions across the beam of no greater than about 2 mm, preferably no greater than about 1 mm diameter. One moving, or a number of stationary similarly-sized radiation detecting elements are placed against the skin surface, most advantageously on the opposite side of the body portion involved, to detect the nonionizing visible and infrared radiation which traverses the region of the body under test. Where a plurality of stationary radiation detecting elements are used, they are preferably very closely spaced to maximize the resolution of the detection measurement. In such case, the outputs of the radiation detecting elements are scanned in synchronism with the movement of the radiation beam so that the output of the detecting elements can be utilized to form an image of the region of the body under test.

As previously indicated, it was discovered that non-cancerous tumors, like those commonly found in benign breast tumors, transmit near infrared radiation wavelengths which are absorbed by cancerous tissue to a greater degree than normal healthy tissue. The physical basis for imaging rests on differential absorption of visible and infrared wavelengths by different kinds of tissues such as fat and blood; and on differential absorption by different states of tissue such as oxidized and reduced. It is thus possible by utilizing the radiation detected from normal healthy tissue to establish a frame of reference from which measurements obtained from cancerous tumors can be shown on a display as a dark or bright spot relative to the background intensity of the display, while measurements obtained from non-cancerous tissue can be shown in the opposite manner relative to the background intensity of the display. Alternatively, the images for cancerous and non-cancerous tumors could be indicated by a different color on a color cathode ray tube display. In like manner, the various normal tissues such as blood and fat can be displayed in differing colors. Similarly oxygenated blood can be shown as red and reduced blood as dark blue.

In accordance with a further feature of the invention, the images are formed from signals involving a subtraction or ratio between two different radiation measurements. In one form of the invention these measurements are obtained from two different wavelength radiation beams applied to each point of the skin surface scanned, one being absorbed to a maximum degree by cancerous tumors and the other being absorbed to a similar degree, by all tissue types being scanned. In another form of the invention, the combined measurements are the measurements obtained from each beam scanned point of the skin surface and a measurement of a known sample of normal healthy tissue, both measurements being obtained from the same or near identical radiation beam. Data processing, memory, and control means are most advantageously provided for establishing a reference measurement level which establishes a given background intensity for the cathode ray tube display. This reference measurement, for example, could be the measurement obtained when the radiation passes through normal tissue. Tissue transmission data is compared with this reference data. If this comparison indicates a greater energy absorption for the tumor indicating that a cancerous tumor is involved there is generated intensity control signals which reduce the intensity of the cathode ray tube raster display, to produce a black indication. If this comparison indicates a lesser energy absorption than for the healthy tissue, there is generated an intensity control signal which produces the brightening effect on the cathode ray tube display. A preferred cancer detection system utilizes a color cathode ray tube.

Still another aspect of the invention is a detection of the presence of cancerous tumors and distinguishing the same from non-cancerous tumors by detecting the differences in the radiation scatter patterns produced thereby. For example, a single beam of near infrared radiation is directed at a point on the skin surface opposite the region of the expected tumor, and measurements are taken of the magnitude of the radiation received at a number of radiation receiving detectors, one of which is centered opposite the incoming radiation beam and the others are spaced on opposite sides of the same. Thus, for cancerous tumors, the centered radiation detector will receive a minimum amount of radiation, and the adjacent detectors on opposite sides thereof will receive progressively increasing amounts of radiation, up to a certain point. On the other hand, for a non-cancerous tumor, the centered detector will receive a maximum amount of radiation, and the detectors on opposite sides thereof will receive progressively decreasing amounts of radiation up to a given point.

In addition to the simple imaging approaches using direct transmission or near neighbor scatter values, one can do computer aided image reconstruction similar to some degree to that which is performed with computerized axial tomographic (CT) x-ray imaging machines. In the computer aided reconstructive imaging using infrared light, all of the infrared detector elements are receiving light from each known light input point. Each new light input point is mapped to all radiation detectors by a geometric back projection algorithm. Thus one can mathematically reconstruct the exact location and configuration of masses within the tissue which have greater or lesser absorption than the remainder of the tissue. Such imaging can be performed at a number of wavelengths. Images obtained by computer aided reconstruction of 1 wavelength can be combined with images obtained by computer aided image reconstruction at another wavelength. Optimally, 3 wavelength false color computerized tomography infrared imaging is envisioned.

Other aspects of the invention to be described relate to specific apparatus particularly useful in detecting breast cancer tumors, which apparatus will be described and shown in the drawings.

The terms "visible and infrared radiation" used herein means non-ionizing radiation having a wavelength in the range of from about 400 to about 700 nanometers, and in the range from about 700 to about $10^6$ nanometers, respectively. The preferred range is from about 400 nanometers to about 4000 nanometers.

The light sources used in the practice of the invention may include a quartz-halogen tungsten filament projector bulb, a xenon arc lamp, a xenon-mercury arc lamp, light-emitting diodes, tunable lasers, or ordinary incandescent light. The wavelength selection means employed advantageously comprises broad or narrow band thin film optical filters with peaks ranging from about 450 nanometers through about 1350 nanometers at regular intervals. One or more monochromators may also be advantageously used. The light delivery or transmission means employed include flexible fiberoptic bundles, rigid light guides or pipes, said means being capable of transmitting the wavelengths of interest. The detector means used include silicon or germanium photodiodes, photomultiplier tubes, vidicons, and the like.

The foregoing, and other features and advantages of the invention, will become clear from the following description and claims taken in conjunction with the accompanying drawings.

DESCRIPTION OF DRAWINGS

FIG. 2A is a view similar to that shown in FIG. 1 representing a modification of the wavefront progression when interrupted by a cancerous breast tumor;

FIG. 2B is a view corresponding to FIG. 2A where the cancerous breast tumor is spaced a further distance from the beam input point of the breast surface than that shown in FIG. 2A;

FIG. 3 is a view corresponding to FIG. 2A where two nonionizing radiation beams have been applied to spaced points on the surface of the breast to create a pair of radiation wavefronts, each of which can produce two shadowgraph images of two non-aligned cancerous tumors indicated therein when radiation passing through the breast involved is detected on the opposite side thereof from the beam entry side of the breast;

FIG. 4 shows in solid lines the shadow pattern of the radiation energy detected from the solid line wavefront in FIG. 3 and in dashed lines the shadow pattern detected from the dashed line wavefront in FIG. 3;

FIG. 5 is a view in perspective of one physical embodiment of the apparatus of the present invention which may be used to obtain data on wavelength specific transmission of visible and infrared light.

FIG. 8A is a sectional view in the interface plane 8—8 shown in FIG. 7 between one side of a compressed female breast and the flat breast-compressing surface of a non-ionizing radiation scanning means, and shows a form of the invention where the radiation scanning means comprises a number of spaced radiation sources which are electrically energized in sequence.

FIG. 8B is a sectional view in an interface plane between one side of a compressed female breast and the flat breast-compressing surface of a non-ionizing radiation beam scanning means, and shows a form of the invention where a mechanical beam scanning means replaces the electronic scanning means of FIG. 7 and includes a single radiation beam source which is physically moved in a pattern across the breast surface, analogously to the scanning of the screen of a cathode ray tube by an electron beam;

FIG. 9A is a sectional view in the interface plane 9—9 shown in FIG. 7 between the opposite side of the compressed female breast and the flat breast-compressing surface of a radiation detector means and shows the radiation detector means in a sectional view as a group of closely spaced detector elements used to detect the radiation transmitted through the female breast involved;

FIG. 9B is a sectional view in the interface plane between the opposite side of the compressed female breast last referred to and the flat breast-compressing surface of a radiation detector means and shows the radiation detector means as comprising a single detector element which scans the adjacent face of the female breast in synchronism with the movement of the single radiation beam source shown in FIG. 8B;

FIGS. 10A and 10B, respectively, show the radiation energy variations detected at adjacent detecting points centered with respect to the point at which the radiation beam enters the female breast, for cancerous and non-cancerous breast tumors, respectively, the minimum point in the curve of FIG. 10A and the maximum point in the curve of FIG. 10B being that detected at a point directly opposite the entry point of the radiation beam into the breast involved;

FIG. 11 is a view in perspective, partly broken away, illustrating an embodiment of a rectilinear scanner head for practicing the present invention;

FIG. 12 is an exploded view, partly in section, of a beam delivery unit for supporting and transmitting radiation through a human breast;

FIG. 15 is a block diagram of a cancer detection system of the invention wherein each point of the body skin surface to be scanned by a radiation beam is quickly scanned in succession by radiation beams having different wavelengths and wherein the image of the breast involved is produced from subtracted measurements of the energy detected from the two radiation beam sources referred to in a manner to optimally differentiate the images from cancerous and non-cancerous tumors;

FIG. 16 illustrates the cancerous and non-cancerous tumor images produced in a black and white image producing cathode ray tube by the cancer detection system of FIG. 15;

FIG. 18 is a block diagram of a cancer detection system of the invention wherein each body skin surface point to be interrogated is scanned sequentially by three beams of different wavelength and where a color display is provided on the face of a color cathode ray tube from radiation detection measurements of the various wavelengths respectively applied to the different color inputs of a color cathode ray tube.

FIG. 19 is a block diagram of a cancer detection system of the invention similar to FIG. 18 except that a different radiation beam array is utilized.

DESCRIPTION OF EXEMPLARY FORMS OF THE INVENTION SHOWN IN THE DRAWINGS

As previously indicated, because of scattering and absorption of the non-ionizing radiation in human tissue, like female breasts, it was heretofore thought practically impossible to obtain useful imaging by transmission of such radiation through female breasts or the like to produce useful measurements or indications which could identify the location and type of tumors present in female breasts. Unexpectedly, I have found that images can be produced of breast tumors of such small size that they are not yet feelable, and which indicates to the observer whether or not such tumors are cancerous or non-cancerous. To best understand the invention, it would be helpful first to review what I believe to be the manner in which a very small non-ionizing radiation beam impinging upon the skin surface of a breast or the like progresses through the breast tissue. Thus, referring now to FIG. 1, a small beam 2 (e.g. about 1 mm. in diameter) impinging upon a point 3 of the skin of one side of a flattened female breast 5 produces, due to scattering effects, a progressing wavefront identified by isoluminance lines $4a, 4b, \ldots 4z$. If, as shown, there are no tumors in the female breast involved, the homogeneity of breast tissue results in a smooth wavefront producing a detectable amount of radiation energy emerging from the opposite side 3' of the breast. In the application of my invention to tumor detection in female breasts, the breast is compacted or squeezed between spaced flat parallel surfaces formed by the flat outer surfaces of radiation scanning and detecting means to be described. The isoluminance lines in FIG. 1, while initially being of a somewhat sinusoidal shape, are believed progressively to approach a shape falling along the curvature of a sphere, as illustrated.

Figure 1:
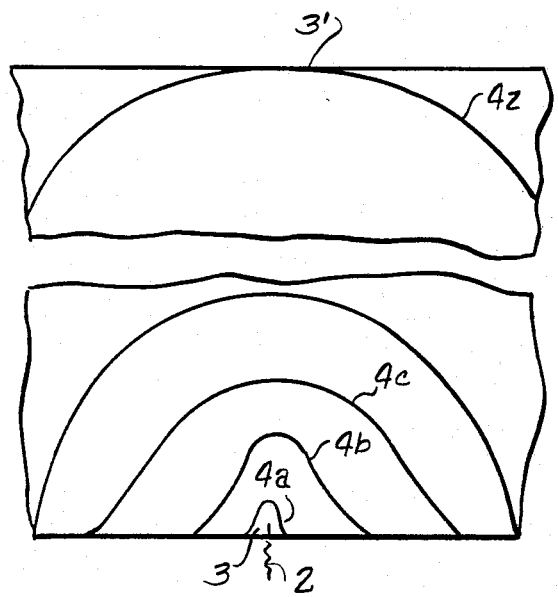
FIG. 1 is a broken-away cross-section through female breast tissue devoid of any tumors, and illustrating the effect of the interaction of a visible or infrared radiation (sometimes to be referred to as the non-ionizing radiation) beam impinging upon a small point of the breast surface and scattered by the tissue to provide a radiation beam wavefront traversing the breast and indicated by isoluminance lines.

When the progressing wavefront of the radiation is interrupted by a cancerous tumor 7 shown in FIG. 2A, which has completely different absorption and scattering characteristics from the fatty breast tissue, the shape of the isoluminance lines will then be modified from that shown in FIG. 1. Because of the radiation measurements which I have made, it is believed that the isoluminance line like $4e'$ immediately beyond the cancerous tumor 6 will have a relatively deep depression 7 formed therein. This depression becomes more shallow as the wavefront progresses to the opposite side of the breast. However, using well known radiation detection means and circuits sensitive to the wavelengths previously identified, even a very shallow depression in the wavefront can be detected. The closer the tumor is to the side of the breast from which the wavefront emerges, the greater the reduction in radiation will be detected at the surface of the breast in line with the entry point of the radiation beam into the breast. Thus, FIG. 2B illustrates a cancerous tumor 6' located a lesser distance from the skin surface point 3 of the breast 5 than shown in FIG. 2A, where the radiation intensity detected at the breast surface 3' will be reduced to a much greater degree than that in the case of the tumor 6 of FIG. 2A (assuming an identical tumor is involved). Note that FIG. 2B shows a deep depression in isoluminance line 4z just beyond the tumor 6' near the skin surface 3' from which the scattered beam emerges.

Figure 2C:
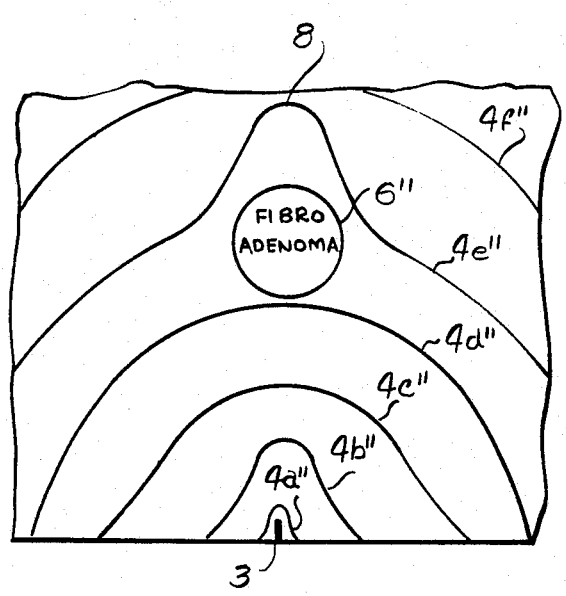
FIG. 2C is a view corresponding to FIG. 2B where the breast tumor is of a non-cancerous variety, such as a fibroadenoma tumor.

Because cancerous and non-cancerous tissue have substantially different characteristics, I concluded that it would be possible not only to detect the presence of tumors in female breasts, but also whether such tumors were cancerous or non-cancerous. Thus, cancerous tumors are characterized by an increased growth rate, increased metabolic rate, increased blood supply, increase in the number and in the size of veins in the region of the tumor, and the presence of microcalcification, in comparison to non-cancerous tumors. These characteristics of cancerous tumors create distinguishing scattering and absorption characteristics. Thus, FIG. 2C illustrates that a non-cancerous tumor 6", such as a fibroadenoma tumor of the breast, produces less absorption relative to normal breast fatty tissue to produce a projection 8 rather than a depression in the isoluminance lines beyond the non-cancerous tumor 6". Accordingly, the detection of an increase of the radiation detected at a point on the female breast in line with the entry point of the radiation beam, as compared to the radiation detected on opposite sides of this point, indicates the presence of a non-cancerous tumor, like a fibroadenoma breast tumor.

It is important for maximum sensitivity of the detection operation of my invention that the wavelength or wavelengths selected for the radiation beam source be that which produces a large differentiation between the normal tissue involved, such as the fatty tissue of the breast, and a cancerous tumor.

FIG. 3 is a view of isoluminance lines produced in a section of tissue 30 having two different cancerous tumors 32 and 34, when the non-ionizing radiation beam is introduced at two points 36 and 38 on the skin surface of the breast involved. The isoluminance lines emanating from point 36 are shown in broken lines, while the isoluminance lines emanating from the point 38 are shown in solid lines. The lines 36a, 36b and 36c emanating from the point 36 provide, as before, a depression 40 which is detectable. However, the isoluminance lines 36a, 36b, and 36c also fan out laterally in the direction of the tumor 34 and form a depression 42 which is detectable as a shadow of the tumor 34 as represented by 34' in FIG. 4. Similarly, isoluminance lines 38a, 38b, 38c, 38d, and 38e emanating from point 38 provide a detectable depression 44 as a result of the absorption of the light by the tumor 34. The shadow 34a thus produced is detectable as represented in FIG. 4. As in the case of the isoluminance lines emanating from point 36, the isoluminance lines 38a, 38b, 38c, 38d, and 38e from point 38 are intercepted and absorbed by the tumor 32 to provide a depression 46 which is detectable as a shadow 32' as shown in FIG. 4. FIG. 4 shows the shadow patterns of the radiant energy detected from the energy at the opposite side of the breast from the solid and dashed line wavefronts of FIG. 3. Thus, it is possible not only to detect the presence of the two tumors 32 and 34 in the tissue 30, but, also, to precisely pinpoint the areas in the tissue 30 where they are located, by back projection computer tomography techniques.

The description to follow describes exemplary apparatus for carrying out various aspects of the invention shown in the various figures previously described. Reference should now be made to FIG. 5 which shows equipment used to prove the basic efficacy of the present invention by providing data indicating the magnitude of the radiation detected when a single non-ionizing beam of a selectable wavelength range is directed through a breast and detected by a single detecting element on the opposite side thereof.

As illustrated in FIG. 5 there is provided a light source and wavelength selection unit 50 connected by a flexible fiber-optic bundle or light guide 52 to a radiation transmitting head 66. A photosensor carrying assembly 54 is connected by a cable 56 to a digital photometer readout unit 58. The light source and wavelength selection unit 50 includes a housing 50a in which a source of infrared light such as a quartz halogen tungsten lamp (not shown) is positioned. A variable intensity control knob 50c is provided on the housing 50a for controlling the intensity of the beam emitted by the lamp. A filter wheel 60 is rotatably mounted on the housing 50a by a shaft 50b. The wheel 60 desirably comprises a plurality of concentrically arranged broad band, thin film interference filters 60a each advantageously having a different peak ranging from 450 nanometers to 1350 nanometers at 50 nanometer intervals. Narrow band filters may be employed to further discriminate among processes detected with the apparatus. The entrance facet 52a of the fiber-optic light guide 52 is maintained in position with respect to the lamp and a selected one of the filters 60a by a collar 62 joined to a standard 64 attached to the base of the housing 50a.

The photosensor carrying member 54 as illustrated comprises a short, stationary end post 54a and a long, stationary end post 54b maintained in fixed, spaced apart relation by a pair of smooth surfaced rods 54c—54c and an externally threaded rod 54d having an adjusting knob 54j. A movable post 54e is positioned between the posts 54a and 54b, and is adjustable in either direction on the rods 54c—54c and 54d by turning the knob 54e. A suitably scaled measuring device 54f is secured at its ends to the stationary posts 54a and 54b. An indicator 54g is secured to the movable post 54e, and is adapted to slide along the markings on the device 54f as the post 54e is moved. The outlet end of the fiber-optic light guide 52 passes through a bore in the outer end of the movable post 54e, and is secured in the disc-shaped head 66. A set screw 68 maintains the outlet end of the guide 52 in position with relation to the post 54e. The long stationary post 54b has an adjustable head 54h which carries a photosensor in the form of a solid-state photodetector 70 of the silicon photodiode type. The head 54h is provided with a knurled adjusting screw 54i to enable the photodetector 70 to be aligned with the outlet end of the fiber-optic light guide 52. The input cable 56 connects the photodetector 70 to the digital photometer readout unit 58. The readout unit 58 has selection buttons 58a for determining the display factors which are visible through a window positioned over a liquid crystal display 58b.

Figure 6:
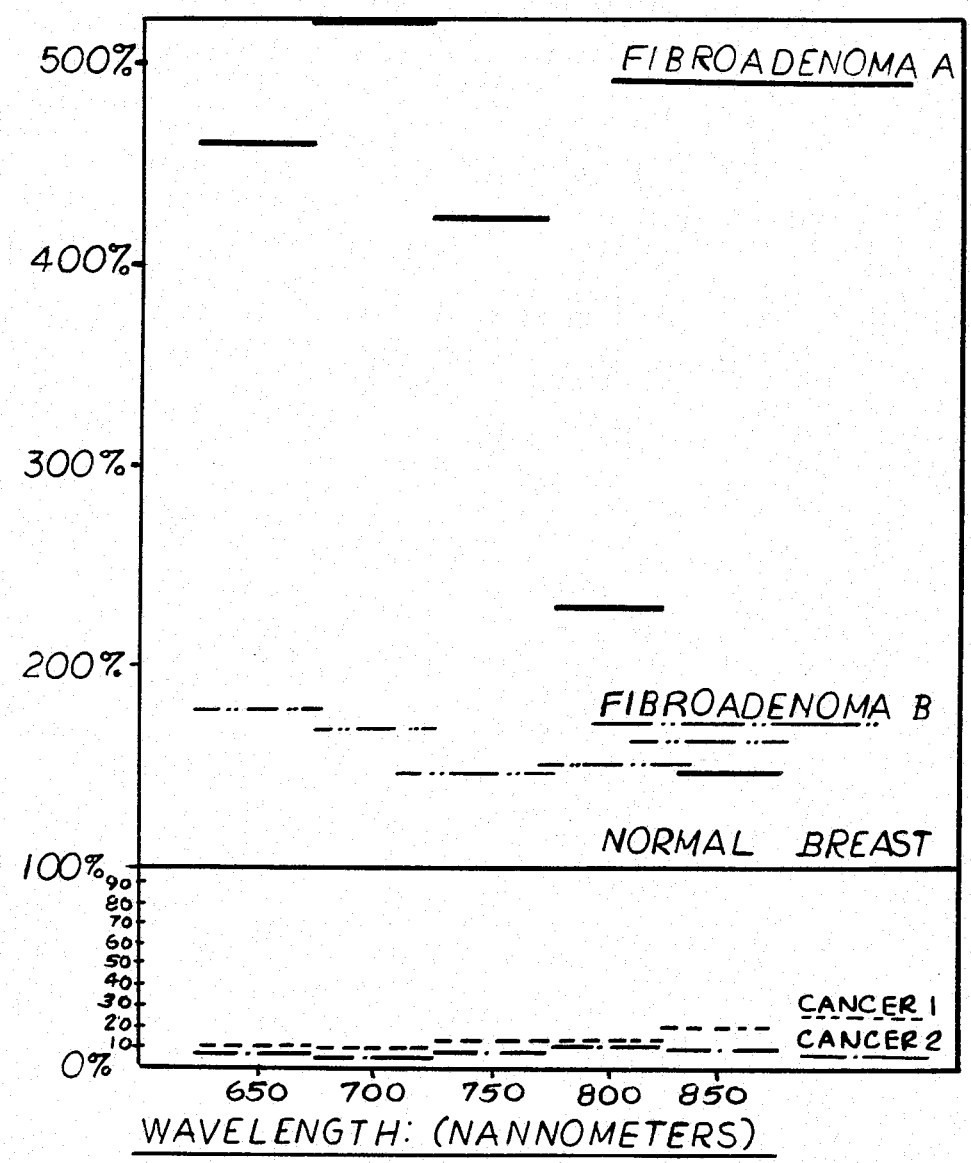
FIG. 6 is a chart illustrating the amount of nonionizing radiation detected by a detector positioned opposite the point where the radiation beam enters the breast.

In utilizing the apparatus shown in FIG. 5, a human breast having a palpable lump is comfortably compressed between the disc 66 and the photodetector 70. The measuring device 54f will indicate the exact distance between the outlet end of the light guide 52 and the photodetector 70, and, therefore, the thickness of the tissue being traversed by the radiation from the source located in the housing 50a. Readings are obtained on the readout unit 58 by passing radiation, at different wavelengths, from the source through the lump in the breast. Using the same wavelengths, light from the source is then passed through an area, or areas, of the breast away from the lump. Since the degree of light scattering and light absorption by a cancerous body is far more intense than that of benign bodies and healthy fatty tissue, the nature of the palpable lump can readily be ascertained from the information displayed by the readout unit 58. The test results of FIG. 6 were obtained from equipment like that shown in FIG. 5. FIG. 6 illustrates the effect of varying the center wavelength of a 50 nm wavelength wide window of a radiation source and shows actual results obtained from patients having both non-cancerous fibroadenoma tumors and typical cancerous tumors of the female breast. Both cancers 1 and 2 exhibit transmissions of less than 20% of normal breast from 650 to 800 nanometers. Both fibroadenomas A and B exhibit much higher than normal transmission, approximately 510% and 170% of normal respectively at 700 nanometers. It is expected that much additional data about various cancers and various benign lumps will be gathered by interrogating tissues with 3 nanometer increments of wavelength, rather than with 50 nanometer increments.

Figure 7:
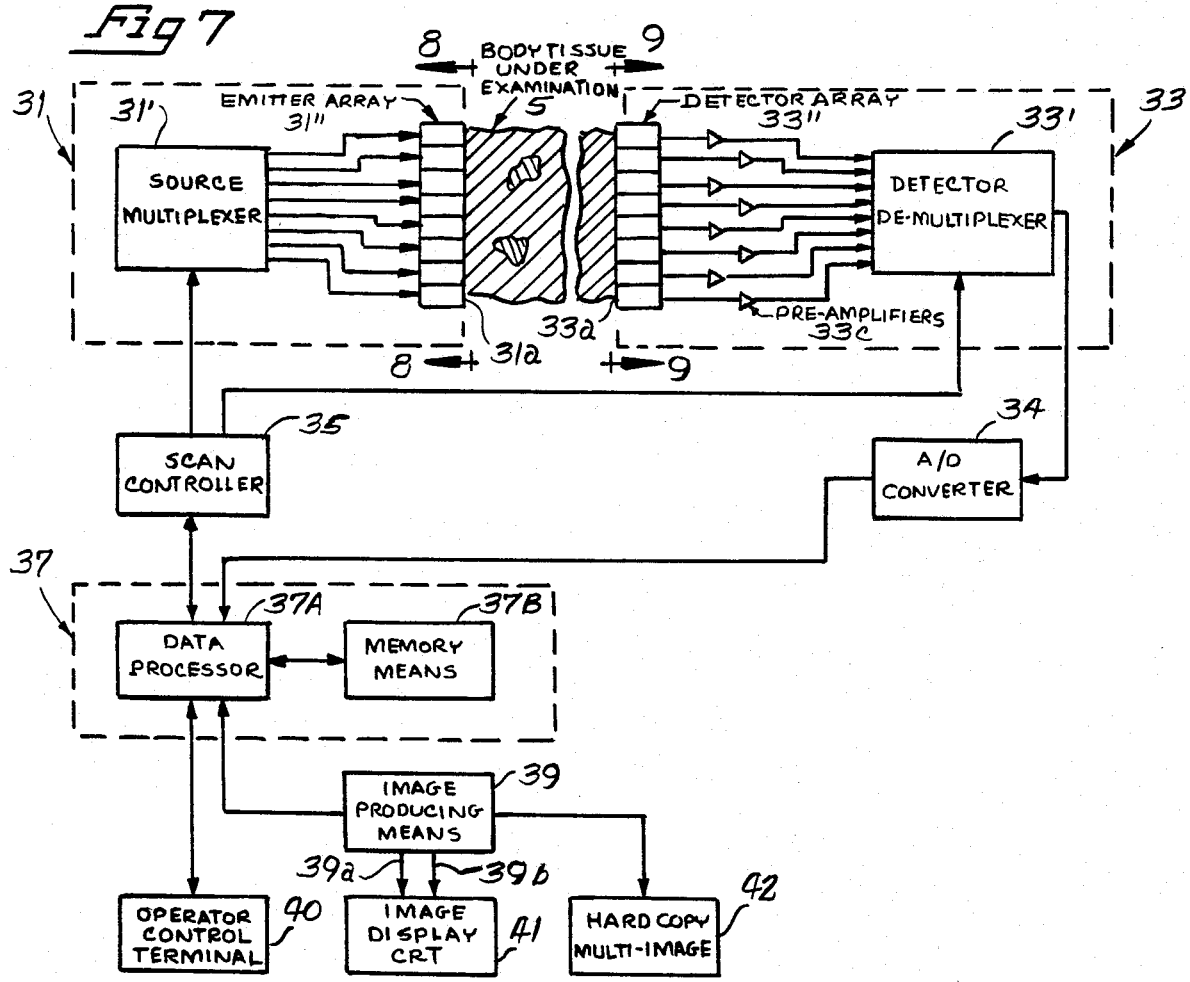
FIG. 7 is a block diagram of an electronic scanner for producing transmission images of human breast or other tissues, using nonionizing radiation.

Refer now to FIG. 7 which illustrates in a simplified block diagram form a basic tumor detection system useful for detecting cancer in the female breast, or in other similar environments, where obtainment of images of tumors, by passing nonionizing radiation through the portion of the body involved, is practical.

There are some organs such as the thyroid where transmission of nonionizing radiation from the skin overlying the thyroid and detection in the back of the neck is not ideal because of the tremendous thickness of organs which are not of diagnostic interest compared with the thinness of the organ which one is attempting to examine. The presence of bone, air containing structures, major blood vessels, and other anatomic components complicates the image interpretation. Nonionizing radiation transmits well through bone. Nonetheless, the complexity of an image formed by many components which are not of diagnostic interest superimposed on the area which is of diagnostic interest raises the desirability of examining certain organs in a reflection mode rather than in a transmission mode. The thyroid is a good example of a tissue in which wavelength specific absorption and scattered phenomena are best recorded in the reflection mode.

FIG. 7 shows a female breast 5 compacted between the flat confronting surfaces 31a and 33a respectively of nonionizing radiation source and scanning means 31 and a radiation detecting and scanning means 33. The radiation source and scanning means 31 may include a source multiplexer 31' which electronically energizes selected radiation sources in an array 31'' of such source. The radiation detecting and scanning means may include a radiation detector array 33'' coupled through preamplifiers 33c and a detector de-multiplexer 33'' for switching a selected preamplifier output. Scanning control means 35 controlling the means 31 and 33 causes a small beam of the nonionizing radiation to progressively scan a selected area of the female breast and radiation detecting and scanning means 33 detects radiation emanating from each point of the female breast which is directly opposite the point at which the radiation beam enters the female breast. The output of the radiation detecting and scanning means 33 is fed through an analog to digital converter 34 to the input of a data processer 37. The data processing, memory and control means 37 feeds the detected data to memory means 37b and generates control signals fed to image displaying means 39 which suitably direct deflection and intensity controls signals to lines 39a and 39b leading respectively to the deflection and intensity control terminals of what is shown as cathode ray tube display means 41. A map or shadowgraph of the radiation detected by the radiation detecting and scanning means 33 is then displayed on the face of a cathode ray tube or other suitable display means.

The data processing, memory and control means 37 is most advantageously provided with circuits for establishing a reference measurement level which establishes a given background intensity for the cathode ray tube display. This reference measurement, for example, could be the measurement obtained when the radiation passes through normal tissue. Tissue transmission data is compared with this reference data. If this comparison indicates a greater energy absorption for the tumor indicating that a cancerous tumor is involved there is generated intensity control signals which reduce the intensity of the cathode ray tube raster display, to produce a black indication. If this comparison indicates a lesser energy absorption than for the healthy tissue, there is generated an intensity control signal which produces the brightening effect on the cathode ray tube display 41. A preferred cancer detection system utilizes a color cathode ray tube to be later described in connection with FIGS. 17, 18, and 19. FIG. 7 also shows an operator control terminal 40 for enabling an operator to control the equipment operation and to select, for example, a hard copy printout, if desired, by a printout means 42 of the cathode ray tube image.

FIGS. 8A and 9A illustrate a portion of the radiation source and scanning means 31 and radiation detecting and scanning means 33, respectively. In this form of the invention, electronic scanning of the female breast is achieved by having a suitable pattern, such as aligned rows and columns, of radiation sources 31b' and radiation detector elements 33b'. In the preferred form of the invention for maximum resolution, the beam produced by the radiation sources 31b' are preferably no more than about 2 millimeters across each dimension, and preferably only about 1 millimeter across each dimension, and are spaced apart a distance approximately equal to these preferred dimensions, as illustrated in FIG. 8B. On the other hand, the radiation detector elements 33b' are preferably in contiguous relation and also preferably of the same size as the beam produced by the radiation sources 31b'.

The radiation sources 31b' and the radiation detecting elements 33b' may be of integrated circuit construction formed on silicon chip or amorphous deposited silicon substrates. Also, switching circuitry is associated therewith so that the rows and columns of radiation sources 31b' are sequentially energized to apply a nonionizing beam to the surface of the breast at progressively varying points along the X and Y axes of the area of the breast to be examined by the apparatus of the present invention.

The manner in which the outputs of the radiation detecting elements 33b' are scanned may vary depending upon the particular application of the invention. For example, if the scanning system being described is to be equivalent to those shown in FIGS. 8B and 9B, then only the correspondingly positioned radiation sources and detector elements are activated synchronously. On the other hand, for more sophisticated applications of the invention, it may be helpful to obtain measurements which are utilized to reconstruct different kinds of shadowgraphs or images. For example, as each radiation source 31b' is activated, in addition to a measurement taken of the output of the correspondingly positioned detecting element, measurements are also taken of the adjacent detecting elements in all directions in order to have a measurement of tissue scattering.

In the most sophisticated version of this invention, all of the radiation detector elements in FIG. 9A are activated at the time that each discrete radiation source 31$b'$ is activated. Data from all detectors is stored in conjunction with information as to which radiation source caused that shadow pattern. With such data in computer memory, back projection reconstruction can be performed mathematically to produce a cross sectional image similar to that produced in computerized axial tomography with X-rays.

The electronic radiation source and scanning means 31 and radiation detection and scanning means 33 in FIG. 7 could be replaced by the mechanical scanning system of FIGS. 8B and 9B.

Referring now to FIG. 8B, the radiation source and scanning means 31 thereshown comprises a masked radiation source 31$b$ which is physically moved back and forth along an X axis at a high rate of speed, and along a Y axis at a slower rate of speed, analogous to the pattern of movement of the electron beam of a cathode ray tube producing a television picture or the like. Accordingly, the radiation source 31$b$ is shown carried on a suitable support frame 31$c$ in turn mounted upon a suitable rotating screw 31$d$ to produce a back and forth movement along the X axis of the radiation source 31$b$. The screw 31$d$, in turn, is supported on a frame 31$e$ mounted upon a rotating screw 31$f$ producing a back and forth movement of the frame 31$e$ along the Y axis.

FIG. 9B illustrates one of the radiation detecting and scanning means 33 which is identical to the radiation source and scanning means 31 except that the radiation source 31$b$ is replaced by a radiation detector element 33$b$ which is moved along the X and Y axes described in synchronism with the radiation source 31$b$ along these axes.

FIGS. 10A and 10B illustrate an application of the invention where the presence or absence of a cancerous or non-cancerous tumor is determined by examining the pattern of radiation measurements obtained from adjacent radiation detector elements centered opposite the activated radiation source. Where a cancerous tumor is aligned with the activated radiation source being described, a depressed curve W1 shown in FIG. 10A is obtained by measurements of the outputs of these radiation detecting elements 33$b'$ along any axis. Thus, a minimum measurement is obtained at point P' by the radiation detecting element 33$b'$ aligned with the radiation source 31$b'$. FIG. 10B illustrates a peaked curve W2 obtained from measurements of the outputs of a group of radiation detector elements 33$b'$ centered with respect to a non-cancerous tumor, like a fibroadenoma tumor. The peak P2 of the curve W2 shown in FIG. 10B is detected by the radiation detecting element 33$b'$ centered with respect to the non-cancerous tumor and the activated radiation source 31$b'$.

Referring, now, to FIG. 11 of the drawings, the embodiment of the invention provides for the mechanical scanning of a female breast. The equipment illustrated, and designated generally by reference numeral 80, comprises a lower, stationary portion 80$a$ and an upper movable portion 80$b$ which is vertically adjustable with relation to the portion 80$a$. The portions 80$a$ and 80$b$ at one end define a pair of transparent parallel plate members 82 and 84 between which a human breast to be examined is compressed. The lower portion 80$a$ of the scanner head 80 is provided with a housing 80$c$ in which is positioned a source of infrared light such as a quartz halogen bulb 86 associated with a reflector 88. A rotatable filter wheel 90 is mounted on a shaft above the bulb 86 and the reflector 88. The wheel 90, like the wheel 60 of the apparatus shown in FIG. 5, is designed to house a plurality of concentrically arranged narrow or broad band optical filters 90$a$ in cavities along its perimeter. An area of the wheel 90 extends through a recess or slot formed in the rear wall of the scanner to enable an operator to readily select any desired filter 90$a$ for tissue interrogation purposes. Light from the bulb 86 passes through a selected filter 90$a$ and enters the entrance end of a flexible fiber-optic bundle 92 held in position on the housing 80$c$ by a fitting 80$d$. The exit end of the optic bundle 92 is secured in a coupling 94$a$ positioned on the upper end of a post 94. The coupling 94$a$ also receives the entrance facet of a rigid light pipe 96 which slides in an alignment member 98 and which terminates at the upper surface of the adjustable upper transparent plate member 80$b$ of the scanner head 80 with which it is in sliding engagement. The exit facet 96$a$ of the light pipe 96 advantageously is provided with a variable aperture (not shown) to enable the diameter of the light beam traversing the optic bundle 92 and the light pipe 96 to be regulated at the exit facet 96$a$ of the light pipe 96. Positioned below and in opposed relation to the exit facet 96$a$ of the light pipe 96 is a photoreceptor 100 provided with a variable aperture 100$a$ for controlling the diameter of the light beam entering the photoreceptor 100. The photoreceptor 100 desirably is a silicon photodiode positioned in sliding engagement with the bottom surface of the lower transparent plate 82 and is mounted on the end of an alignment shaft 102.

The shaft 102 passes through a bore in an alignment member 104 and is received in an integral coupling 94$b$ provided at the lower end of the post 94. The coupling 94$b$ is secured to an internally grooved sleeve 106 which receives an externally grooved drive shaft 108. The shaft 108 is driven by a motor 104$a$ carried by the alignment member 104, and is grooved to form a combined clockwise and counterclockwise helix such that, upon completion of its travel in either direction along the drive shaft 108, the sleeve 106 will automatically reverse its direction of travel. As the shaft 108 rotates, the post 94, the light pipe 96 and the photoreceptor 100 are simultaneously moved in the direction of travel of the sleeve 106. At each fore and aft travel end point, the increased resistance by the sleeve 106 to rotation of the shaft 108 causes a precise increase in the rotation of a gear shaft 110 carried on the alignment member 104. Each end of the gear shaft 110 is provided with a gear 110$a$—110$a$ which travel on parallely arranged gear tracks 112—112. Thus, a two dimensional surface can be interrogated by the fore and aft, and lateral travel of the exit facet 96$a$ of the light pipe 96 and photoreceptor 100 in response to the motion of the drive shaft 108 and the gear shaft 110. The various portions of a breast compressed between the plate members 82 and 89 are thus scanned by the scanning movement imparted to the light pipe 96 and photoreceptor sliding in alignment together along the surfaces of transparent plate members 82 and 89 so that the breast is scanned without any sliding contact being made with it.

Figure 13A:
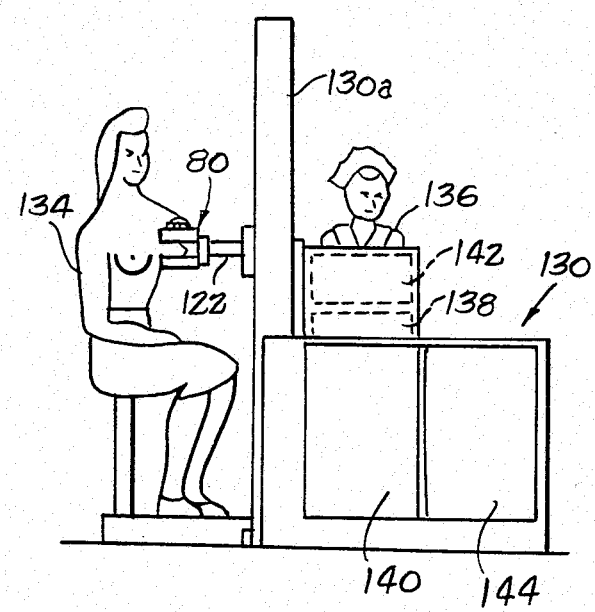
FIGS. 13A and 13B are side and top views, respectively, of an embodiment of apparatus utilizing a rectilinear scanner head of the type shown in FIG. 11 in conjunction with a cathode ray tube set up for interrogating the human breast.
Figure 13B:
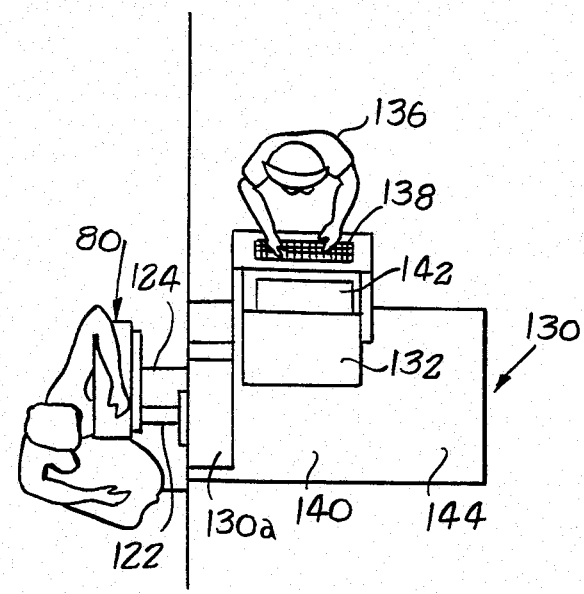

Alignment of the movable elements of the head 80 is maintained by the alignment parallely arranged tracks 114 and 116, respectively. The entire upper portion 80$b$ of the scanning head 80 can be moved vertically relative to the lower portion 80$a$ so as to accept substantially any size breast. The post 94 and the shaft 110 are splined to allow free up and down movement from a distance of about one inch to four inches. A motor driven toothed power transmission belt is connected to height adjustment screws (not shown) positioned at the corners of the scanning head 80 to enable the space between the clear plastic surfaces of the members 82 and 84 to be adjusted as desired. A shaft 122 provided for connecting the scanning head 80 to a scanning console 130 (see FIGS. 13A and 13B). A cable 124 carries two sets of electronic signals to the imaging console 132. One set of signals relates to the absolute intensity of light sensed by the photoreceptor 100. The other set of signals relates to the absolute XY positional coordinates of the light pipe exit facet 96a and the photoreceptor variable aperture 100a. These sets of electronic signals provide intensity modulation to a CRT beam and location control to that beam. As shown in FIGS. 13A and 13B, the breast of a patient 134 is compressed in the scanning head 80 which is connected by the shaft 122 to a support column 130a. An operator 136 communicated by a keyboard 138 with the control electronics 140 to produce an image and alpha-numeric display on cathode ray tube 142. Images on photographic film are produced by a multiformat imager 144.

In FIG. 12 of the drawings, there is shown a sophisticated female breast scanning head where the radiation source is stationary. The apparatus comprises a base member 150 and a breast supporting member 152. The member 150 carries a light source such as a quartz halogen bulb (not shown) positioned in a reflector 154. A filter wheel 156 is rotatably mounted above the reflector 154 and is provided with a plurality of optical filters 156a concentrically arranged around the perimeter thereof. A portion of the outer margin of the wheel 156 extends outwardly through a slot 150a formed in the side wall of the member to facilitate rotation of the wheel. A light pipe 158 having a light entrance facet positioned adjacent to the filter wheel 156 in opposed relation to the light source is carried in the member 150. The light pipe 158 is branched to provide two light exit facets 158a and 158b which are shadowed by a toothed aperture wheel 160. The light pipe 158, its light exit facets 158a and 158b, and the aperture wheel 160 rotate about a hollow shaft 162 driven by a belt 164 connected to a drive disc 166 and a motor 168. The member 152 is provided with a downwardly extending rod 152a which is received in the hollow shaft 162 of the member 150. The member 152 is contoured to enable a patient to be comfortably examined. The upper surface 152a of the member 152 has a plurality of evenly spaced light projection aperture points or orifices 152b formed therein and arranged along equally spaced concentric circles of progressively increasing diameter about a central light point. Each of the orifices 152b is aligned with the light exit facets 170a of an equal number of fiber-optic light delivery bundles 170. The light entrance facets 170b are arranged adjacent spaced rows of openings 152c formed in the bottom surface of the member 152. In operation, the light exit facets 158a and 158b of the light pipe 158, and the apertured wheel 160 are rotated in a manner such that the outer and inner rows of openings 152c, and their associated light entrance facets 170b of the optic bundles 170, are addressed sequentially. A timing signal from the motor 168 is fed to a computerized axial tomographic apparatus 180 (see FIGS. 14A and 14B).

Figure 14A:
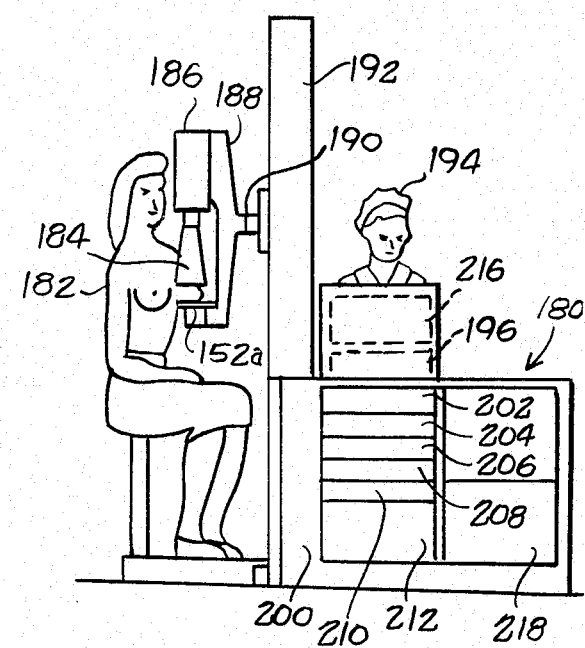
FIGS. 14A and 14B are side and top views, respectively, illustrating the light delivery unit shown in FIG. 12 used in conjunction with computerized tomography apparatus for interrogating a human breast.
Figure 14B:
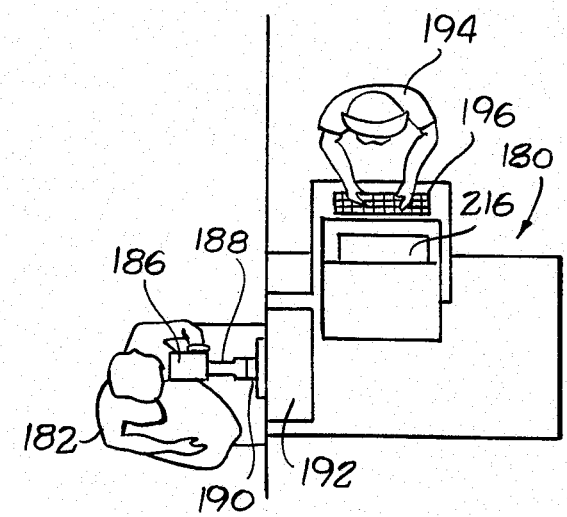

As shown in FIGS. 14A and 14B, a patient 182 is seated with her left breast compressed between the upper surface 152a of the member 152 and a light excluding cone 184. The computerized axial tomographic apparatus schematically illustrated comprises image receptor means which includes a computer compatible tv camera 186. A yoke 188 maintains optical alignment. A shaft 190 allows rotation about the horizontal axis and vertical movement is possible along a support column 192. An operator 194 manipulates a keyboard 196 for communicating with the computer and to display images and alpha-numerics on a cathode ray tube. Computer system 200 consists of several modules including a video analog-digital converter 202, a camera-computer interface 204, and a frame storage unit 206. The frames 208 are operated upon by a uniformity connection module 210, and are passed to frame memory 212. When the family of images coded to the light points from exit facets 170a of the member 152 have been acquired, an image reconstruction algorithm 214 operates upon these frames to create a computer reconstructed back projected image. This image is displayed on a television image display monitor 216, and is simultaneously displayed on a high resolution video screen of a multiformat film imager 218 which serves to produce transparency images of the breast on the member 152 similar in appearance to conventional mamograms. The computerized axial tomographic embodiment can be used in conjunction with multiple wavelengths such as are illustrated in FIGS. 15, 17, 18 and 19.

Refer now to FIG. 15 which illustrates a form of the invention for increasing the sensitivity of the tumor detection system of the invention when applied to provide a shadowgraph image on a cathode ray tube or other similar display device. In this form of the invention, a pair of nonionizing radiation sources 31B and 31B' are provided. Radiation source 31B is selected so that it is absorbed to a much greater degree by cancerous tumors than by non-cancerous tumors and normal healthy tissue. Radiation source 31B', on the other hand, is selected so that it is absorbed to a similar degree by tumors and normal healthy tissue. The radiation sources 31B and 31B' may be stationary sources fed to a more or less conventional beam chopper 35' controlled by a beam chopper control means 42 which alternately couples the radiation beam from the radiation source 31B an 31B' to a suitable mechanical scanner 31c which alternately applies the output of the beam chopper 35' to progressively varying points on the skin surface involved. Radiation detector scanning means 33c is provided which may be the same as scanner 31c and operates in synchronism to the scanner 31c to couple the radiation received at the various skin surface points involved to a radiation detector 33b whose output is coupled through an analog to digital converter 34 to a data processor 37A. The data processor 37A effects the storing of those measurements obtained from the outputs of the detecting elements resulting from the beam radiation source 31B to memory means 37b, and the storing of the measurements obtained from the outputs of the detecting elements resulting from the beam radiation source 31B' to memory means 37c. The data processor 37A also feeds the data from memory means 37b and 37c obtained from each of the two beams directed to a given point on the skin surface involved to a subtracting means 37d which subtracts the measurements involved. These results of this subtracting function are directed to the subtracted data memory means 37e' which stores this subtracted data for each of the points scanned in succession by the beams from the radiation sources 31B and 31B'.

The data for each scanned point in subtracted data memory means 37e' is fed to comparator means 44 which senses whether or not the subtracted data involved is positive or negative. If the computation is negative, indicating the cancerous tumor, a blanking initiating signal is fed on a line 4a' extending to the data processor 37A which, in turn, feeds a blanking signal on a line 37b to image producing means 39' associated with an image display means 41, which may be a black and white cathode ray tube. The data processor 37A also feeds deflection control signals on a line 37b' to the image producing means 39'.

The image producing means 39' has an intensity control output line 39b and a deflection control output line 39b' respectively extending to intensity control input terminal 41b and deflection control input terminal 41b' of the cathode ray tube 41. The aforementioned blanking signal will cause a black image to appear on the face of the cathode ray tube 41 at the position thereof representing a cancerous tumor. The deflection control and intensity signals fed to input terminals 41b and 41b' will produce an image of the region of the body scanned in a manner like that previously explained.

When the comparator means 44 senses a positive measurement indicating normal healthy tissue or non-cancerous tumors, a signal indicating this fact is fed by detector means 44 on line 44a' to the data processor 37A which then effects feeding of a signal varying with the actual value of the subtracted data involved fed from the data memory means 37e' to the data processor which, in turn, feeds intensity control signals on the line 37b to the image producing means 39' which produces a gray scale image producing signal of a value proportional to the magnitude of the subtracted data in the memory means 37e'. In such case, non-cancerous tumors which absorb less radiation than normal healthy tissue will produce intense or bright images relative to the background display identifying normal healthy tissue, in the case of the scanning of a female breast.

The various functions, like the subtracting and the detecting functions, carried out by the boxes depicted in FIG. 15 and other figures as well, can be carried out by hardware components separate from the data processor 37A or could be incorporated as software within the data processor 37A.

With such a cancer detection system as described, a visual presentation of the scanned breast area may be something like that shown in FIG. 16, where non-cancerous tumors will appear as bright spots or areas S1 and cancerous tumors will appear as dark spots or areas S2. The image can be light-dark reversed if desired.

Figure 17:
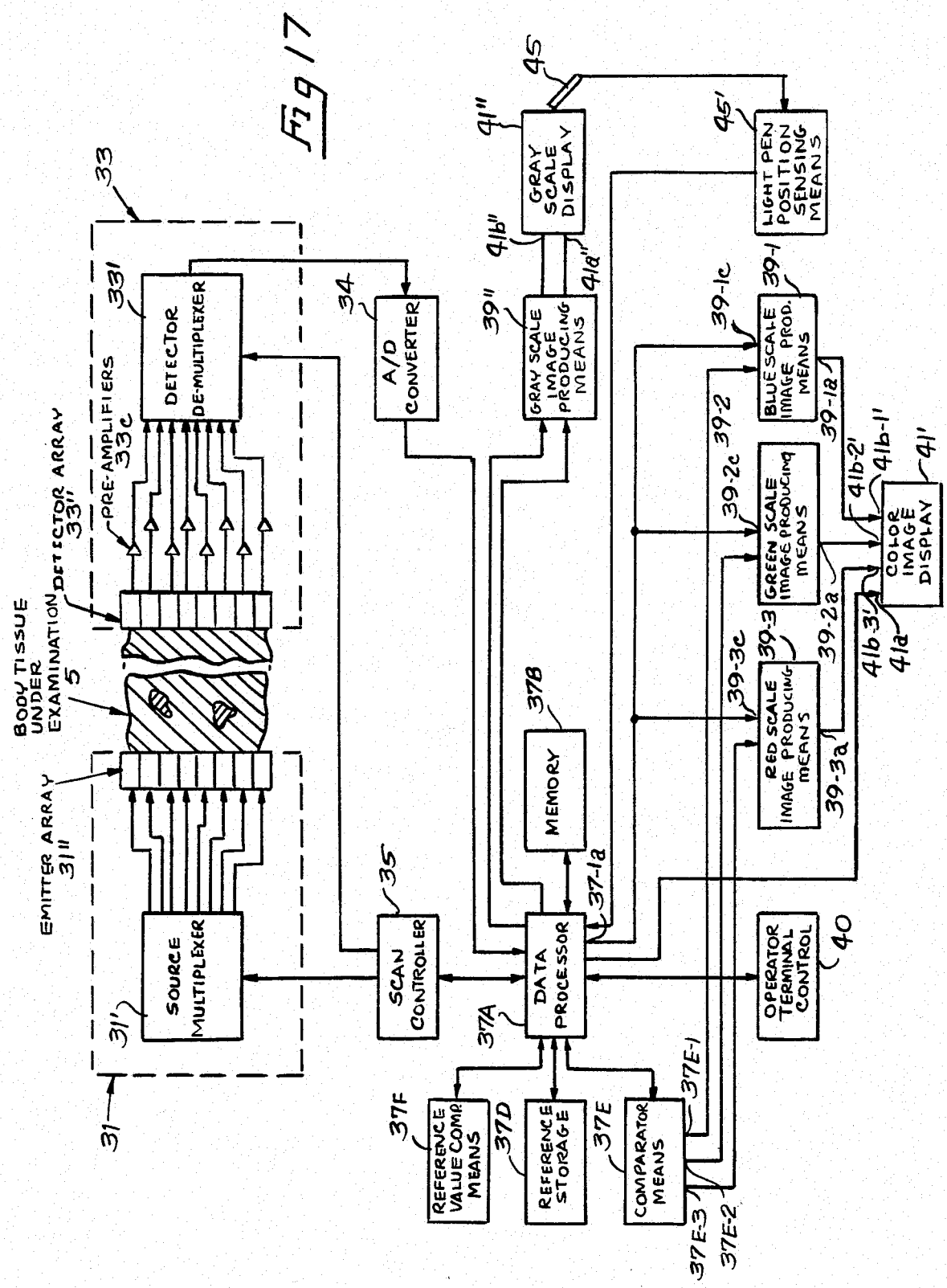
FIG. 17 is a block diagram of a cancer detection system of the invention wherein an emitter array is sequentially actuated to apply sequentially a beam of one wavelength to each skin surface point to be interrogated and wherein a color display is provided on the face of a color cathode ray tube from measurements of the radiation detected at various skin surface points compared with a reference measurement obtained from normal healthy tissue, an image of one color identifying a cancerous tumor and an image of another color identifies a non-cancerous tumor.

Refer now to FIG. 17 which shows a cancer detection system which operates with a color image display means 41' which may be a cathode ray tube having blue, green and red beam intensity control input terminals 41b-1', 41b-2' and 41b-3' respectively, and a deflection control input terminal 41a. The input terminals 41b-1', 41b-2' and 41b-3' respectively are connected to intensity signal output terminals 39-1a, 39-2a and 39-3a of blue, green and red image producing means 39-1, 39-2 and 39-3. Intensity control input terminals 39-1b, 39-2b and 39-2c of the image producing means 39-1, 39-2 and 39-3 are connected to output terminals 37E-1, 37-E2 and 37-E3 of a comparator means 37E. (It should be understood that, in some instances, single lines in the block diagram of the drawings represent multiple lines which couple multi-bit binary signals.) Deflection control input terminals 39-1c, 39-2c and 39-3c of the image producing means 39-1, 39-2 and 39-3 are respectively connected to deflection signal terminal 37-1a of the data processor 37A.

In the cancer detection system shown in FIG. 17, a reference measurement which represents the mean value of normal healthy tissue in an area selected by the operator is obtained. There is then compared with this mean measurement data obtained from the various portions of the breast (or other portion of the body scanned) and any such measurement which exceeds this mean value, for example, by two "standard deviations" (which is a term well known in the statistics field) will be displayed as a green image on the cathode ray tube. Any data which falls below this mean value by the same two standard deviations will be displayed thereon as a red image and any data falling within the range of the mean value plus or minus two standard deviations will be displayed thereon as a blue image, which will constitute the background color of the cathode ray tube picture.

The cancer detection system shown in FIG. 17 has therein various basic components corresponding to those shown in FIG. 7, and these corresponding sectional components have been shown by similar reference numbers like 31, 33, 34 and 35 respectively representing the radiation source and scanning means 31, radiation detecting and scanning means 33, analog to digital converted and scanning control means 35. These means develop the data signals to be fed to data processor 37A and memory means 37B. The data processor 37A controls the feeding of the data from the outputs of the radiation detector elements involved to suitable storage locations of the memory means 37B associated with the different scanned points of the breast or other portion of the body involved.

To determine the mean value referred to, a light pen 45 commonly used in data processing systems is provided in association with a black and white cathode ray tube 41". This cathode ray tube has a deflection control input terminal 41a" and an intensity control input terminal 41b" coupled to the output of image producing means 39" which receives uncompensated data input signals and position or deflection control signals from data processor 37A. An image of the breast region scanned is thereby produced on the face of the cathode ray tube 41" where the intensity or degree of grayness of the images produced corresponds to the magnitude of the radiation detected by the radiation detecting elements of the radiation detection and scanning means 33.

The light pen 45 or the like is moved by the operator along an outline of a desired area containing normal healthy tissue on the face of the cathode ray tube 41". In any manner well known in the art, the light pen 45 develops signals identifying the area marked by the movement of the pen, which signals are fed to a light pen position sensing means 45', in turn coupled, to the data processor 37A responsive thereto. The data processor will then effect the feeding of data from memory means 37B of the data for the breast region outlined by the movement of the light pen 45 over the face of the cathode ray tube 41" to a reference value computing means 37F which computes this mean value which is stored in reference storage means 37D. The data processor 37A also controls the feeding of data on all of the points scanned (i.e. not limited to the area selected by the light pen 45) from memory means 37B to comparator means 37E at the appropriate time. The comparator means 37E compares the mean value computed by reference value computing means 37F with this data from each point scanned and produces signals respectively on output terminals 37E-1, 37E-2, and 37E-3 thereof when the comparison operations show that the data from the scanned point involved is respectively (a) within the range of the mean value plus or minus two standard deviations, (b) greater than the mean value plus two standard deviations, and (c) less than the mean value minus two standard deviations. These output terminals are respectively connected to the blue, green and red image producing means 39-1, 39-2 and 39-3 to activate the imaging means 39-1, 39-2 or 39-3 depending upon which output terminal 37E-1, 37E-2 or 37E-3 contains a signal indicating the result of the comparison operation carried out by the comparator means 37E. In this way, an appropriately colored image is provided on the cathode ray tube 41' at a position on the face thereof which corresponds with the position of the radiation beam applied to the breast skin surface. The data processor 37A may be designed to provide a back projection computer tomographic image on the cathode ray tube 41' utilizing conventional computer techniques used in x-ray produced images. It should be noted, however, that it is unexpected that shadowgraph or computer tomographic images of the breast area can be obtained from nonionizing radiation like that described since such a result does not necessarily follow from the fact that such images can be produced by x-rays which are not scattered within the tissue interrogated as in the case of the nonionizing radiation utilized in the present invention, and so the present invention produces unexpected and surprising results having advantages over x-ray technology for the reasons previously explained.

FIG. 18, which shows components corresponding to similarly numbered components in FIGS. 7 and 17, illustrates a false color multi-spectral imaging embodiment of the invention. As there shown, each point in the tissue is rapidly scanned by 3 discrete wavelength beams from radiation sources 31B, 31B' and 31B''. The multi-spectral false color imaging can be performed with varying degrees of computer image enhancement including smoothing digital filtering, and back projection processing. Radiation source 31B provides a wavelength #1 which is fed through beam chopper 35' to the scanner 31c where the radiation traverses the portion of the body involved. The radiation is detected by the detector and scanning means 33. Information is then fed through the analog to digital converter 34 to data processor 37A synchronized with the scan controller 35. In a similar fashion, radiation source 31B' of wavelength #2 and radiation source 31B'' of wavelength #3 are fed through the beam chopper 35', scanner 31c, and body portion and detected by detector and scanning means 33 to provide data for the data processor 37A. The data derived from wavelengths #1, #2, and #3 are respectively stored in data memory means 37b, 37c and 37d. Data in each of these memories may be normalized by data processor 37A. (Normalization is a well known technique used in cathode ray tube data display systems where a given range of data values obtained from a scanning of variable data is converted to a modified range of values varying over a predetermined range). The data processor 37A feeds the data stored in memory means 37b, 37c and 37d respectively to the blue, green and red color image-producing inputs 39-1c, 39-2c and 39-3c of image producing means 39 (shown as one box rather than three separate boxes as in other figures). The image producing means 39 has red, green and blue image producing signal output terminals 39-1a, 39-2a and 39-3a coupled to corresponding intensity control input terminals of the cathode ray tube 41' for producing superimposed multi-color images of the scanned tissue.

FIG. 19 shows a multi-spectral false color imaging system similar to the imaging system of FIG. 18 except that electronic scanning rather than mechanical scanning means is utilized. Thus, a triple source multiplexer 31' is provided which sequentially activates the individual radiation emitting devices of a visible or infrared radiation emitter array 31''. This array preferably comprises adjacent clusters of 3 radiation emitting devices, the radiation devices in each cluster emitting toward the same skin surface location three different wavelength beams which are differentially absorbed or scattered by cancerous, non-cancerous and normal healthy tissue, as in the case of the three radiation sources in the embodiment of the invention in FIG. 18. The triple source multiplexer 31' is controlled by scan controller 35 and data processor 37A so that the devices are sequentially scanned in any desired sequence. Thus, the three devices of each cluster of devices can be sequentially scanned in immediate sequence, following which another or adjacent cluster of such devices are similarly scanned. Alternatively, the corresponding radiation emitting devices of the different clusters can be scanned in immediate sequence. Thus, there is a time separation of the different wavelength beams emitted by the array 31'', so that the detected radiation beam measurements can be processed and stored in appropriate storage locations of the memory means 37b, 37c and 37d. In other respects the imaging system of FIG. 19 operates in the same manner as imaging system of FIG. 18 and thus, a further description of FIG. 19 will not be made.

It should be understood that, especially for detection of breast tumors, the radiation wavelengths which produce the best results fall in the range of from about 600 to about 900 nanometers. For other applications radiation wavelengths in the visible range of from about 400 to about 700 nanometers and in the infrared range from 700 nanometers to about 1 millimeter are useful, depending upon the tissue environment involved.

In all of the embodiments of the invention including FIGS. 18 and 19 just described, it should be understood that the cancer detection systems illustrated therein can utilize light pen techniques to provide reference measurements to be integrated with the other described measurements, or for other desirable purposes. Also, the various cancer detection systems are preferably provided with hard copy multi-imaging means like imaging means 42 in FIG. 15 for producing a permanent record of the image appearing on the cathode ray tube face involved.

It should also be noted that the functions carried out by the blocks in the figures previously described can be carried out by either hardware completely, or by a combination of hardware and software. In most applications electronic scanning and mechanical scanning are interchangeable. The present invention is obviously not limited to the particular details of how the well known individual functions carried out by the blocks of the diagrams are actually carried out.

While the invention has been disclosed and described with relation to its utilization in the detection of human breast lesions, it should be understood that the invention can also be used to monitor the changing optical absorption and scatter characteristics of light in other accessible tissues of the body. While transmission imaging has been extensively described, reflection imaging is equally feasible and is preferred for thyroid imaging.

What is claimed is:

1. A method of detecting the presence of tumors and distinguishing cancerous from non-cancerous tumors in situ within the body of a human being or animal, said method comprising the steps of scanning a test region in said body by individually applying at discrete locations on the skin surface of said body opposite the test region in said body where a tumor may be located a visible or infrared beam of radiation having a tumor-distinguishing wavelength which is absorbed or scattered to a greater degree by a cancerous tumor relative to a non-cancerous tumor and by surrounding normal healthy tissue and which is absorbed or scattered to a lesser degree relative to a non-cancerous tumor than by normal healthy tissue and cancerous tumors, and detecting and measuring the magnitude of the radiation emanating from the skin surface of the body at a discrete point of the skin surface no greater than 2 mm thereacross on the opposite side of the test region where the radiation is expected to emanate for each individual application of radiation as the radiation being directed into the skin surface irradiates said region of the body where a tumor may be located and determining from said detecting and measuring if any tumors are present and if present distinguishing cancerous from non-cancerous tumors.

2. A method of detecting cancerous female breast tumors in situ within the body of a human being, said method comprising the steps of scanning a test region in said body by individually applying to various discrete points of the skin surface of said body opposite the test region in said body where a tumor may be located a visible or infrared beam of radiation having dimensions no greater than about 2 mm thereacross and having a tumor-distinguishing wavelength which is absorbed or scattered to a much greater degree by a cancerous tumor than by surrounding normal healthy breast tissue, detecting the radiation at discrete points of the skin surface on the opposite side of the breast where the radiation beam is expected to emanate from the breast after interrogating the test region thereof to obtain measurements identifying the presence of cancerous tumors.

3. A method of claims 1 or 2 wherein said tumor-distinguishing wavelength is from about 600 to about 900 nanometers.

4. A method of detecting tumors in situ within the body of a human being or animal, said method comprising the steps of scanning a test region in said body by individually applying to discrete points of the skin surface of said body opposite the test region in said body where a tumor may be located a visible or infrared beam of radiation having dimensions no greater than about 2 mm thereacross and having a tumor-distinguishing wavelength which is absorbed or scattered to a much different degree by a tumor than by surrounding normal healthy tissue, detecting the radiation at discrete points of the skin surface where the radiation beam is expected to emanate from the skin surface after interrogating the test regions of the body, to obtain measurements identifying the presence of tumors and forming from such detected radiation an image of the region scan where the color, intensity or darkness of the different areas of the image is a function of the magnitude of the radiation detected at said discrete points.

5. The method of claim 2 or 4 wherein said wavelength of said radiation is absorbed or scattered by cancerous and non-cancerous tumors respectively to opposite degrees relative to normal healthy tissue, obtaining a reference measurement of the radiation absorbed or scattered by normal healthy tissue (which distinguishes the measurement obtained from said tumor-distinguishing wavelength) comparing each measurement of the detected radiation from said discrete points of the skin surface from which said radiation emanates with respect to said reference measurement, and providing an image which provides an indication of the relative positions of said tumors and normal healthy tissue and provides a distinguishing indication for cancerous tumors and non-cancerous tumors.

6. The method of claim 1 or 4 wherein said beam of radiation is directed on the skin surface of one side of said body and is detected at a point on the skin surface on the other side of said body opposite the point of entry of said radiation beam into said body, and providing measurements with spatial information from the detected radiation.

7. The method of claims 1, 2 or 4 wherein for each discrete point of said skin surface receiving a radiation beam there is also detected at a number of radiation detecting points where the beam of radiation emanates from said skin surface the magnitude of the radiation received thereat, and producing an indication of the variations of the magnitude of the radiation detected at said number of radiation detecting points.

8. The method of claims 1, 2 or 4 wherein for each discrete point of said skin surface receiving a radiation beam there is also detected at a number of radiation detecting points where the beam of radiation emanates from said skin surface the magnitude of the radiation received thereat, and producing a computer tomographic reconstruction image from the variations of the magnitude of the radiation detected at said number of radiation detecting points.

9. The method of claim 2 or 4 wherein, in addition to applying said tumor-distinguishing wavelength beam to each of the beam receiving discrete points of said skin surface, there is also applied to each such point at least another beam having a different wavelength which is absorbed to a similar degree by tumors and normal breast tissue, and further detecting and measuring the magnitude of the radiation emanating from the discrete points of the skin surface resulting from said beam of said different wavelength beam and obtaining modified measurements by subtracting or forming a ratio between the radiation measurements received at each of said discrete points, and forming said image from said modified measurements.

10. The method of claim 2 or 4 wherein, in addition to applying said tumor-distinguishing wavelength beam to each of said discrete beam-receiving points, there is also applied to each such point a second and a third beam having substantially different wavelengths from each other and said tumor-distinguishing wavelength and which respectively are absorbed to a similar degree by tumors and normal breast tissue and to a substantially different degree for cancerous and non-cancerous tumors and detecting and measuring the magnitude of the radiation emanating from said discrete beam emanating points of the skin surface resulting from said second and third as well as the first mentioned beam, and forming from said measurements superimposed images of contrasting color to each other.

11. A method of detecting the presence of tumors and distinguishing cancerous from non-cancerous tumors in situ within the body of a human being or animal, said method comprising the steps of directing at different points on the skin surface of said body opposite the test region in said body where a tumor may be located a first visible or infrared radiation beam having a tumor distinguishing wavelength which is scattered or absorbed to different degrees by a cancerous tumor, a non-cancerous tumor and normal healthy tissue, and a second visible or infrared radiation beam having a wavelength which will be absorbed to near the same degree by cancerous and non-cancerous tumorous and normal healthy tissue, detecting and measuring the magnitude of the radiation resulting from said first and second radiation beams emanating from different points on the skin surface of the body after the radiation beams involved have irradiated said region of the body where a tumor may be located, obtaining modified measurements by subtracting or forming a ratio with the measured magnitudes of radiation emitted from said different points so that the differences in the resulting measurements are due primarily to the specific wavelength absorption or scattering effects from tumors involved, and forming from such modified measurements images of the regions interrogated where the color, intensity or darkness of the different areas of the image distinguishes the tumors from normal healthy tissue and cancerous from non-cancerous tumors.

12. The method of claim 11 wherein said radiation wavelength is scattered or absorbed to opposite degrees by cancerous and non-cancerous tumors, respectively, relative to the absorption or scattering thereof by normal healthy tissue, and forming from said modified measurements images where cancerous and non-cancerous tumors are shown by different indications relative to each other and from the indications for normal healthy tissue.

13. The method of claims 1, 2, 4 or 10 wherein said visible or infrared radiation beam at the entrance thereof into the skin surface has dimensions across the beam no greater than about 2 mm in any direction thereacross.

14. The method of claims 1, 2, 4 or 10 wherein the area of said skin surface over which the emanating radiation beam is detected has dimensions no more than about 2 mm in any direction across the area.

15. The method of claims 1, 2, 4 or 10 wherein said visible or infrared radiation beam at the entrance thereof into the skin surface has dimensions across the beam no greater than about 2 mm in any direction thereacross and the area of said skin surface over which the emanating radiation beam is detected has dimensions no more than about 2 mm in any direction across the area.

16. The method of claims 11 or 12 wherein said method is applied to a female breast where the beam of radiation is directed on the skin surface of one side of the breast and is detected at a point on the skin surface thereof on the opposite side of the breast from the point of entry of said radiation beam into the same.

17. Apparatus for detecting the presence of tumors and for distinguishing cancerous from non-cancerous tumors in situ within the body of a human being or animal, said apparatus comprising means for scanning a test region in said body by individually directing at discrete points on the skin surface of said body opposite the test region in said body where a tumor may be located a visible or infrared beam of radiation having dimensions no greater than about 2 mm thereacross and having a tumor-distinguishing wavelength which is absorbed or scattered to a much greater degree by a cancerous tumor than by a non-cancerous tumor and by normal healthy tissue, and which is absorbed or scattered to a lesser degree by a non-cancerous tumor than by a cancerous tumor and by normal healthy tissue and means for detecting and measuring the magnitude of the radiation emanating from the skin surface of the body as the radiation beam directed into the skin surface irradiates said region of the body where a tumor may be located to obtain measurements identifying the presence of tumors and distinguishing cancerous from non-cancerous tumors.

18. Apparatus for detecting tumors in situ within the body of a human being or animal, said apparatus comprising means for scanning a test region in said body by individually applying to discrete points of the skin surface of said body opposite the test region in said body where a tumor may be located a visible or infrared beam of radiation having dimensions no greater than about 2 mm thereacross and having a tumor-distinguishing wavelength which is absorbed or scattered to a much different degree by a tumor than by normal healthy tissue, means for detecting the radiation at discrete points of the skin surface where the scanning radiation beam is expected to emanate from the skin surface after interrogating the test regions of the body, to obtain measurements identifying the presence of tumors and means for forming from such detected radiation an image of the region interrogated where the color, intensity or darkness of the different areas of the image is a function of the magnitude of the radiation detected at said discrete points and which image distinguishes tumors from normal healthy tissue.

19. Apparatus for detecting female breast cancerous tumors in situ within the body of a human being, said apparatus comprising means for scanning a test region in said breast by individually applying to various discrete points of the skin surface of said breast opposite the test region in said breast where a tumor may be located a visible or infrared beam of radiation having dimensions no greater than about 2 mm thereacross and having a tumor-distinguishing wavelength which is absorbed or scattered to a much greater degree by a cancerous tumor than by surrounding normal breast tissue and non-cancerous tumors, means for detecting the radiation at discrete points of the skin surface where the radiation beam is expected to emanate from the skin surface after interrogating the test regions of the body, and means for forming from such detected radiation an image of the region interrogated where the color, intensity or darkness of the diffrent areas of the image is a function of the magnitude of the radiation detected at said discrete points and which image distinguishes cancerous tumors from normal healthy tissue and non-cancerous tumors.

20. Apparatus for detecting the presence of tumors and distinguishing cancerous from non-cancerous tumors in situ within the body of a human being or animal, said apparatus comprising means for scanning a test region in said body by individually directing at different points on the skin surface of said body opposite the test region in said body where a tumor may be located a first visible or infrared radiation beam having a tumor-distinguishing wavelength which is scattered or absorbed to a greater degree by a cancerous tumor than by a non-cancerous one or by surrounding normal healthy tissue and to a lesser degree by a non-cancerous tumor than by surrounding normal healthy tissue, and a second visible or infrared radiation beam having a wavelength which will be absorbed to near the same degree by cancerous and non-cancerous tumorous and normal healthy tissue, means for detecting and measuring the magnitude of the radiation resulting from said first and second radiation beams emanating from different points on the skin surface of the body after the radiation beams involved have irradiated said region of the body where a tumor may be located, means for obtaining modified measurements by subtracting or forming a ratio with the measured magnitudes of radiation emitted from said different points so that the differences in the resulting measurements are due primarily to the specific wavelength absorption or scattering effects from tumors in the tissue involved, and means for forming from such modified measurements images of the regions interrogated where the color, intensity or darkness of the different areas of the image distinguish the tumors from normal healthy tissue and cancerous tumors from non-cancerous tumors.

21. The tumor-detecting apparatus of claims 18 or 19 wherein said radiation beam has a wavelength in the range of from about 600 to 900 nanometers.

22. The tumor-detecting apparatus of claims 17, or 20 wherein said near infrared or infrared radiation beam has dimensions across the beam no greater than about 2 mm in any direction thereacross.

23. The tumor-detection apparatus of claims 7, 18, 19 or 20 wherein said detecting means includes one or more detecting elements each having radiation detecting surfaces having dimensions no more than about 2 mm in any direction across the area.

24. The tumor-detecting apparatus of claims 17, or 20 wherein said near infrared or infrared radiation beam has dimensions across the beam no greater than about 2 mm in any direction thereacross and the said detecting means includes detecting elements each having radiation detecting surfaces having dimensions no more than about 2 mm in any direction across the area.

25. The tumor-detection apparatus of claim 18 or 19 wherein said tumor-distinguishing wavelength is absorbed or scattered in opposite degrees relative to normal healthy tissue by cancerous and non-cancerous tumors and there is provided means for obtaining a reference measurement for the amplitude of the radiation passing through or reflected within the body for normal healthy tissue, means for comparing the measurement of the tumor-distinguishing radiation detected by said detecting and measuring means for each beam which passes through or is reflected within the body portion involved with said reference measurement, and means responsive to the compared measurement for providing a distinguishing indication identifying cancerous and non-cancerous tumors.

26. The tumor-detecting apparatus of claim 17, 18, 19 or 20 wherein there is provided storage means for storing each measurement of the radiation emanating from each skin surface point, means for obtaining and storing a reference measurement different from that produced by the measurement of said tumor-distinguishing wavelength and indicative of the degree of radiation scattered or absorbed from normal healthy tissue, said reference measurement being one which falls between tumor-distinguishing radiation measurements for cancerous and non-cancerous tumors, first display means, and means for comparing each stored tumor-distinguishing radiation measurement and said stored reference measurement and forming on said first display means an image which distinguishes between normal healthy tissue, cancerous and non-cancerous tumors.

27. The tumor-detecting apparatus of claim 26 wherein said reference measurement obtaining means includes a display means, and means for producing from the measurements of the tumor-distinguishing radiation at said skin surface points an image of the interrogated portion of said body, and there is provided pointer means movable by the user over any selected part of the last mentioned display means to select a normal healthy tissue area thereof, and means for storing the radiation measurement of the part of the body selected by the positioning of said pointer means.

28. The tumor detecting apparatus of claim 27 wherein the last mentioned display means is a black and white cathode ray tube; and there is provided a color cathode ray tube including first, second and third signal input terminals for providing differently colored indications on the face of the color cathode ray tube; and said image-forming means including means responsive to the comparison of said stored reference measurement and the stored measurements obtained from said tumor-distinguishing radiation which indicates a non-cancerous tumor for feeding a signal to one of said signal input terminals of said color cathode ray tube, responsive to a comparison of said reference measurement and the stored measurements obtained from said tumor-distinguishing radiation which indicates normal healthy tissue for feeding a signal to another of said signal input terminals of said cathode ray tube, and responsive to a comparison of said reference measurement and the stored measurements obtained from said tumor-distinguishing radiation which indicates a cancerous tumor for feeding a signal to the other signal input terminal of said cathode ray tube.

29. The tumor-detecting apparatus of claim 17 wherein said detecting means includes a detector having a variable aperture.

30. The tumor-detecting apparatus of claim 17 wherein said detecting means comprises a plurality of independent detecting elements forming a detector array.

31. The tumor-detecting apparatus of claim 30 wherein said detecting elements are contiguous so that they are spaced apart a distance less than the dimensions thereacross.

32. The tumor-detecting apparatus of claim 17 or 18 wherein said radiation directing means direct a beam having a wavelength in the range of from about 400 nanometers to about one millimeter.

33. The tumor-detecting apparatus of claim 17 wherein said radiation directing means includes wavelength selection means for varying the wavelength of the beam to select the optimum tumor-distinguishing radiation.

34. The tumor-detecting apparatus of claim 33 wherein said wavelength selection means comprise broad band thin film interference filters having peaks ranging from about 450 nanometers to about 1350 nanometers.

35. The tumor-detecting apparatus of claim 33 wherein said wavelength selection means and filters are carried on a rotatable wheel.

36. The tumor-detecting apparatus of claim 17 wherein said radiation directing means includes radiation transmission means for transmitting radiation from one or more sources of radiation along a predetermined path to the skin surface to be irradiated, said radiation transmission means comprising a flexible fiber-optic filament bundle or a rigid light pipe.

37. The tumor-detecting apparatus of claim 17 wherein there is provided computerized tomography means, responsive to said detecting and measuring means for constructing tomographic images of the interrogated tissue.

38. The tumor-detecting apparatus of claim 17, said beam directing means including a wide range wavelength source of said radiation wavelength selection means through which radiation from said source can be selectively passed, radiation delivery means having a light entrance facet positioned adjacent to the wavelength selection means and a radiation exit facet to be positioned adjacent to human tissue undergoing interrogation.

39. The tumor-detecting apparatus of claim 17, wherein said apparatus is for detecting and locating human breast tumors, said radiation beam directing means includes a wide band source of radiation producing a skin irradiating beam having a wavelength in the range of 400 to about 1400 nanometers.

40. The tumor-detecting apparatus of claim 39 wherein said radiation beam directing means includes a movable filter support having arranged thereon a plurality of broad band thin film interference filters with peaks ranging from about 450 nanometers through about 1350 nanometers at equally spaced nanometer intervals, said support being positioned with relation to said radiation source to enable any selected one of the filters on the wheel to intercept light emitted by said source.

41. The tumor-detecting apparatus of claim 40 combined with a fiber-optic filament bundle having a light entrance facet positioned to receive radiation passing through said any one selected filter and a light exit facet means for delivering filtered light from said source to a breast suspected of having a tumor therein.

42. The tumor-detecting apparatus of claim 19, 39 or 40 wherein one of said radiation directing or applying means and radiation detecting means is relatively movable toward and away from the other of same and provide breast compacting means for flattening the breast therebetween.

43. The tumor-detecting apparatus of claim 18 wherein said tumor-distinguishing wavelength is absorbed to a greater degree by cancerous than by non-cancerous tumors and normal healthy tissue, said beam applying means also applies to each of the discrete beam receiving points near infrared or infrared beams of radiation having second and third wavelengths different from said tumor-distinguishing wavelength, said second wavelength being absorbed to a lesser degree by non-cancerous tumors than by cancerous tumors and normal healthy tissue, said third wavelength being absorbed to a similar degree by cancerous and non-cancerous tumors and normal healthy tissue; said image-forming means comprising a color cathode ray tube having separate input terminals for providing differently colored indications on the screen of the cathode ray tube and having an intensity varying with the amplitude of said signals fed thereto, and means responsive to the magnitude of the radiation detected at each of the discrete beam emanating points resulting respectively from the three different wavelength beams for feeding corresponding signals respectively to said signal input terminals of said cathode ray tube, so that differently colored superimposed images are provided of the tumors and normal healthy tissue of the body portion interrogated.

44. The tumor-detecting apparatus of claim 17 wherein said radiation directing means includes a source of radiation having a variable aperture.

45. The tumor-detecting apparatus of claim 17 wherein said radiation directing means comprises a plurality of independent radiation sources forming a radiation source array.

46. The apparatus of claim 17 wherein said means for detecting comprises a vidicon.

47. A method of detecting tumors in situ within the body of a human being or animal, said method comprising the steps of directing at a given location on the skin surface of said body opposite the test region in said body where a tumor may be located a visible or infrared beam of radiation having a tumor-distinguishing wavelength which is absorbed or scattered to a greater degree by a cancerous tumor relative to a non-cancerous tumor and by surrounding normal healthy tissue and which is absorbed or scattered to a lesser degree relative to a non-cancerous tumor than by normal healthy tissue and cancerous tumors, detecting and measuring the magnitude of the radiation emanating from the skin surface of the body as the radiation beam directed into the skin surface irradiates said region of the body where a tumor may be located to obtain measurements identifying the presence of tumors and distinguishing cancerous from non-cancerous tumors, wherein for each discrete point of said skin surface receiving a radiation beam there is also detected at a number of radiation detecting points where the beam of radiation emanates from said skin surface the magnitude of the radiation received thereat, and producing a computer tomographic reconstruction image from the variations of the magnitude of the radiation detected at said number of radiation detecting points.

48. A method of detecting tumors in situ within the body of a human being or animal, said method comprising the steps of directing at a given location on the skin surface of said body opposite the test region in said body where a tumor may be located a visible or infrared beam of radiation having a tumor-distinguishing wavelength which is absorbed or scattered to a greater degree by a cancerous tumor relative to a non-cancerous tumor and by surrounding normal healthy tissue and which is absorbed or scattered to a lesser degree relative to a non-cancerous tumor than by normal healthy tissue and cancerous tumors, wherein said visible or infrared radiation beam at the entrance thereof into the skin surface has dimensions across the beam no greater than about 2 mm in any direction thereacross, and detecting and measuring the magnitude of the radiation emanating from the skin surface of the body as the radiation beam directed into the skin surface irradiates said region of the body where a tumor may be located to obtain measurements identifying the presence of tumors and distinguishing cancerous from non-cancerous tumors.

49. Apparatus for detecting tumors in situ within the body of a human being or animal, said apparatus comprising means for directing at a given location on the skin surface of said body opposite the test region in said body where a tumor may be located a visible or infrared beam of radiation having a tumor-distinguishing wavelength which is absorbed or scattered to a much greater degree by a cancerous tumor than by a non-cancerous tumor and by surrounding normal healthy tissue, wherein said visible or infrared radiation beam has dimensions across the beam no greater than about 2 mm in any direction thereacross, and means for detecting and measuring the magnitude of the radiation emanating from the skin surface of the body as the radiation beam directed into the skin surface irradiates said region of the body where a tumor may be located to obtain measurements identifying the presence of tumors and distinguishing cancerous from non-cancerous tumors.

50. Apparatus for detecting tumors in situ within the body of a human being or animal, said apparatus comprising means for directing at a given location on the skin surface of said body opposite the test region in said body where a tumor may be located a visible or infrared beam of radiation having a tumor-distinguishing wavelength which is absorbed or scattered to a much greater degree by a cancerous tumor than by a non-cancerous tumor and by surrounding normal healthy tissue, and means for detecting and measuring the magnitude of the radiation emanating from the skin surface of the body as the radiation beam directed into the skin surface irradiates said region of the body where a tumor may be located to obtain measurements identifying the presence of tumors and distinguishing cancerous from non-cancerous tumors, wherein there is provided computerized axial tomography means responsive to said detecting and measuring means for constructing tomographic images of the test region.

51. Apparatus for detecting tumors in situ within the body of a human being or animal, said apparatus comprising means for directing at a given location on the skin surface of said body opposite the test region in said body where a tumor may be located a visible or infrared beam of radiation having a tumor-distinguishing wavelength which is absorbed or scattered to a much greater degree by a cancerous tumor than by a non-cancerous tumor and by surrounding normal healthy tissue, and means for detecting and measuring the magnitude of the radiation emanating from the skin surface of the body as the radiation beam directed into the skin surface irradiates said region of the body where a tumor may be located to obtain measurements identifying the presence of tumors and distinguishing cancerous from non-cancerous tumors, wherein said radiation directing means comprises a plurality of independent radiation sources forming a radiation source array.

* * * * *

UNITED STATES PATENT AND TRADEMARK OFFICE
CERTIFICATE OF CORRECTION

PATENT NO. : 4,515,165

DATED : May 7, 1985

INVENTOR(S) : Robert G. Carroll

Page 1 of 4

It is certified that error appears in the above-identified patent and that said Letters Patent is hereby corrected as shown below:

On the first page of the patent after "References Cited U.S. PATENT DOCUMENTS," please insert:

| | | |
|---|---|---|
| 3,245,402 | 4/1966 | Barnes |
| 3,638,640 | 2/1972 | Shaw |
| 4,077,399 | 3/1978 | Le Roy |
| 4,223,680 | 9/1980 | Jobsis |

After "Alfano.......128/665," please insert:

FOREIGN PATENT DOCUMENTS

| | |
|---|---|
| 987,504 | Great Britain |
| 1,252,470 | Great Britain |
| 1,263,195 | Great Britain |
| 1,318,552 | Great Britain |
| 1,346,486 | Great Britain |
| 1,387,696 | Great Britain |
| 1,401,227 | Great Britain |
| 1,521,113 | Great Britain |
| 1,538,695 | Great Britain |
| 1,559,810 | Great Britain |
| 2,013,878 | Great Britain |
| 0,009,999 | European Patent Application |

UNITED STATES PATENT AND TRADEMARK OFFICE
CERTIFICATE OF CORRECTION

PATENT NO. : 4,515,165

DATED : May 7, 1985

INVENTOR(S) : Robert G. Carroll

It is certified that error appears in the above-identified patent and that said Letters Patent is hereby corrected as shown below:

PUBLICATIONS

"Breast Imaging Techniques", March, 1983, Radiologic Clinics of North America, Vol. 21, No. 1, pgs 149-153.

"Transillumination Light Scanning", Diagnostic Imaging, April, 1982.

"Transillumination of Breast Tissues: Factors Governing Optimal Imaging of Lesions", Radiology, 147:89-92, April, 1983.

"Infrared Photography of Patients", Radiography and Clinical Photography, Vol. 21, No. 3.

"The Infrared Phlebogram in the Diagnosis of Breast Complaints", Surgery, Gyneacology and Obstetrics "Preliminary Report on Transilluminography", February, 1933

"Noninvasive, Infrared Monitoring of Cerebral and Myocardial Oxygen Sufficiency and Circulatory Parameters, Science, Vol. 198, pgs. 1264-1267, December 23, 1977.

UNITED STATES PATENT AND TRADEMARK OFFICE
CERTIFICATE OF CORRECTION

PATENT NO. : 4,515,165
DATED : May 7, 1985
INVENTOR(S) : Robert G. Carroll

It is certified that error appears in the above-identified patent and that said Letters Patent is hereby corrected as shown below:

In the Abstract, line 10, delete "grey" and insert --gray--.

In column 2, line 61, delete "anc" and insert --and--.

In column 11, line 48, delete "33"" and insert --33'--.

In column 11, line 58, delete "processer" and insert --processor--.

In column 15, line 43, delete "152a" and insert --152d--.

In column 16, line 21, delete "mamograms" and insert --mammograms--.

In column 16, line 41, delete "an" and insert --and--.

In column 17, line 3, delete "4a'" and insert --44a'--.

In column 17, line 60, change "37-E2" to --37E-2--; and in line 61, change "37-E3" to --37E-3--.

In column 24, claim 19, line 50, delete "diffrent" and insert --different--.

UNITED STATES PATENT AND TRADEMARK OFFICE
CERTIFICATE OF CORRECTION

PATENT NO. : 4,515,165
DATED : May 7, 1985
INVENTOR(S) : Robert G. Carroll

It is certified that error appears in the above-identified patent and that said Letters Patent is hereby corrected as shown below:

In column 25, claim 23, line 26, change "7" to --17--.

In column 27, claim 43, line 59, delete "the" second occurrence and insert --said--; and in line 60, delete "said" and insert --the--.

Signed and Sealed this

Seventh Day of January 1986

[SEAL]

Attest:

DONALD J. QUIGG

Attesting Officer

Commissioner of Patents and Trademarks